(12) United States Patent
Kharrat et al.

(10) Patent No.: US 9,346,883 B2
(45) Date of Patent: May 24, 2016

(54) ANTIBODIES AGAINST HER3

(75) Inventors: Abdelhakim Kharrat, Montgiscard (FR); Olivier Dubreuil, Mauressac (FR); Yassamine Lazrek, Montpellier (FR); Philippe Mondon, Donneville (FR); Khalil Bouayadi, Ramonville Saint-agne (FR); Thierry Chardes, Assas (FR); Andre Pelegrin, Montpellier (FR); Christel Larbouret, Valflaunes (FR); Nadege A. Gaborit, Metz (FR)

(73) Assignees: INSTITUT NATIONAL DE LA SANTE ET DE LA RECHERCHE MEDICALE (INSERM), Paris (FR); Gamamabs Pharma SA, Toulouse Cedex 1 (FR)

( * ) Notice: Subject to any disclaimer, the term of this patent is extended or adjusted under 35 U.S.C. 154(b) by 0 days.

(21) Appl. No.: 14/116,562

(22) PCT Filed: May 11, 2012

(86) PCT No.: PCT/EP2012/058769
§ 371 (c)(1),
(2), (4) Date: Jan. 31, 2014

(87) PCT Pub. No.: WO2012/156309
PCT Pub. Date: Nov. 22, 2012

(65) Prior Publication Data
US 2014/0141019 A1 May 22, 2014

(30) Foreign Application Priority Data
May 13, 2011 (EP) .................................... 11305583

(51) Int. Cl.
C07H 21/04 (2006.01)
C07K 16/28 (2006.01)
C07K 16/32 (2006.01)

(52) U.S. Cl.
CPC ............. *C07K 16/2863* (2013.01); *C07K 16/32* (2013.01); *C07K 2317/21* (2013.01); *C07K 2317/34* (2013.01); *C07K 2317/76* (2013.01)

(58) Field of Classification Search
None
See application file for complete search history.

(56) References Cited

FOREIGN PATENT DOCUMENTS

| WO | 2007/077028 A2 | 7/2007 |
| WO | 2008/100624 A2 | 8/2008 |
| WO | WO 2008/100624 | * 8/2008 |

OTHER PUBLICATIONS

Rudikoff et al. (Proc Natl Acad Sci USA 1982 vol. 79 p. 1979).*
MacCallum et al. (J. Mol. Biol., 1996, 262: 732-745).*
Xu et al (Immunity, 2000, 13:37-45).*
Casset et al. (BBRC, 2003, 307:198-205).*
Pascalis et al. (The Journal of Immunology, 2002, 169: 3076-3084).*
McKay et al., "Tolerance to single, but not multiple, amino acid replacements in antibody V-H CDR2: A means of minimizing B cell wastage from somatic hypermutation?", Journal of Immunology, Jan. 1, 1996, pp. 3285-3291, vol. 156, No. 9.

* cited by examiner

*Primary Examiner* — Laura B Goddard
(74) *Attorney, Agent, or Firm* — Whitham, Curtis, Christofferson & Cook, P.C.

(57) ABSTRACT

The invention relates to antibodies against HER3 and their use in the treatment of cancer.

12 Claims, 9 Drawing Sheets

SEQUENCE LISTING

<160> NUMBER OF SEQ ID NOS: 36

<210> SEQ ID NO 1
<211> LENGTH: 5
<212> TYPE: PRT
<213> ORGANISM: Homo sapiens

<400> SEQUENCE: 1

Asp Tyr Ala Met His
1               5

<210> SEQ ID NO 2
<211> LENGTH: 16
<212> TYPE: PRT
<213> ORGANISM: Homo sapiens

<400> SEQUENCE: 2

Ile Ser Trp Asn Ser Gly Ser Ile Gly Tyr Ala Asp Ser Val Lys Gly
1               5                   10                  15

<210> SEQ ID NO 3
<211> LENGTH: 11
<212> TYPE: PRT
<213> ORGANISM: Homo sapiens

<400> SEQUENCE: 3

Glu Gly Gln Trp Pro Asn Tyr Gly Met Asp Val
1               5                   10

<210> SEQ ID NO 4
<211> LENGTH: 13
<212> TYPE: PRT
<213> ORGANISM: Homo sapiens

<400> SEQUENCE: 4

Pro Gly Ser Ser Ser Asn Ile Gly Asn Asn Tyr Val Ser
1               5                   10

<210> SEQ ID NO 5
<211> LENGTH: 7
<212> TYPE: PRT
<213> ORGANISM: Homo sapiens

<400> SEQUENCE: 5

Asp Asn Asn Glu Arg Pro Ser
1               5

<210> SEQ ID NO 6
<211> LENGTH: 11
<212> TYPE: PRT
<213> ORGANISM: Homo sapiens

<400> SEQUENCE: 6

Gly Ala Trp Asp Asn Thr Leu Gly Val Tyr Val
1               5                   10

<210> SEQ ID NO 7
<211> LENGTH: 120
<212> TYPE: PRT
<213> ORGANISM: Homo sapiens -continued

<400> SEQUENCE: 7

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gln Trp Pro Asn Tyr Gly Met Asp Val Trp Gly Gln
            100                 105                 110

Gly Thr Thr Val Thr Val Ser Ser
        115                 120

<210> SEQ ID NO 8
<211> LENGTH: 110
<212> TYPE: PRT
<213> ORGANISM: Homo sapiens

<400> SEQUENCE: 8

Gln Ser Val Leu Thr Gln Pro Pro Ser Val Ser Ala Ala Pro Gly Gln
1               5                   10                  15

Lys Val Thr Ile Ser Cys Pro Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Glu Arg Pro Ser Gly Ile Pro Asp Arg Phe Ser
    50                  55                  60

Gly Ser Thr Ser Gly Thr Ser Ala Thr Leu Asp Ile Thr Asp Leu Gln
65                  70                  75                  80

Ala Glu Asp Glu Ala Thr Tyr Tyr Cys Gly Ala Trp Asp Asn Thr Leu
                85                  90                  95

Gly Val Tyr Val Leu Gly Thr Gly Thr Gln Leu Thr Val Leu
            100                 105                 110

<210> SEQ ID NO 9
<211> LENGTH: 360
<212> TYPE: DNA
<213> ORGANISM: Homo sapiens

<400> SEQUENCE: 9
gaggtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atagtggtag cataggctat      180
gcggactctg tgaagggccg attcaccatc tccagagaca cgccaagaa ctcactgtat      240 ctgcaaatga acagcctgag agccgaggac acggctgtgt attactgtgc gagagaaggg     300
cagtggccga actacggtat ggacgtctgg ggccaaggga ccacggtcac cgtctcctca     360

<210> SEQ ID NO 10
<211> LENGTH: 330

```
<212> TYPE: DNA
<213> ORGANISM: Homo sapiens

<400> SEQUENCE: 10
cagtctgtgt tgacgcagcc gccctcagtg tctgcggccc cagggcagaa ggtcaccatc      60
tcctgccctg gaagcagctc caacattggg aataattatg tatcctggta ccagcagctc     120
ccagggacag cccccaaact cctcatttat gacaataatg agcgaccctc aggattcct      180 gaccgattct ctggctccac gtctggcacg tcagccaccc tggacatcac cgacctccag     240
gctgaggacg aggccactta ttattgcggt gcctgggata caccctggg tgtttacgtc      300 ctcggaactg ggacccagct caccgtttta                                      330

<210> SEQ ID NO 11
<211> LENGTH: 13
<212> TYPE: PRT
<213> ORGANISM: Homo sapiens

<400> SEQUENCE: 11

Ser Gly Ser Ser Ser Asn Ile Gly Ser Asp Pro Val Asn
1               5                   10

<210> SEQ ID NO 12
<211> LENGTH: 7
<212> TYPE: PRT
<213> ORGANISM: Homo sapiens

<400> SEQUENCE: 12

Ser Asn Asn Gln Arg Pro Ser
1               5

<210> SEQ ID NO 13
<211> LENGTH: 11
<212> TYPE: PRT
<213> ORGANISM: Homo sapiens

<400> SEQUENCE: 13

Ala Ala Trp Asp Asp Ser Leu Arg Gly Tyr Val
1               5                   10

<210> SEQ ID NO 14
<211> LENGTH: 120
<212> TYPE: PRT
<213> ORGANISM: Homo sapiens

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gln Trp Pro Asn Tyr Gly Met Asp Val Trp Gly Gln
            100                 105                 110
```

Gly Thr Thr Val Thr Val Ser Ser
            115                 120

<210> SEQ ID NO 15
<211> LENGTH: 110
<212> TYPE: PRT
<213> ORGANISM: Homo sapiens

<400> SEQUENCE: 15

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asp
            20                  25                  30

Pro Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Arg Gly Tyr Val Phe Gly Thr Gly Thr Lys Leu Thr Val Leu
            100                 105                 110

<210> SEQ ID NO 16
<211> LENGTH: 360
<212> TYPE: DNA
<213> ORGANISM: Homo sapiens

<400> SEQUENCE: 16
gaggtgcagc tggtggagtc cggggggaggc ttagttcagc ctgggggggtc cctgagactc    60 tcctgtgcag cctctggatt cacctttgat gattatgcca tgcactgggt ccggcaagct   120
ccagggaagg gcctggagtg gtctcaggt attagttgga atagtggtag cataggctat   180
gcggactctg tgaagggccg attcaccatc tccagagaca acgccaagaa ctcactgtat   240
ctgcaaatga acagcctgag agccgaggac acggctgtgt attactgtgc gagagaaggg   300
cagtggccga actacggtat ggacgtctgg ggccaaggga ccacggtcac cgtctcctca   360

<210> SEQ ID NO 17
<211> LENGTH: 330
<212> TYPE: DNA
<213> ORGANISM: Homo sapiens

<400> SEQUENCE: 17
cagtctgtgc tgactcagcc accctcagcg tctgggaccc ccgggcagag ggtcaccatc    60
tcttgttctg gaagcagctc caacatcgga agtgatcctg taaactggta ccagcagctc   120
ccaggaacgg cccccaaact cctcatctat agtaataatc agcggccctc agggtccct   180 gaccgattct ctggctccaa gtctggcacc tcagcctccc tggccatcag tgggctccag   240
tccgaggatg aggctgatta ttactgtgca gcatgggatg acagcctgag gggttatgtc   300
ttcggaactg ggaccaagct gaccgtccta                                      330

<210> SEQ ID NO 18
<211> LENGTH: 13
<212> TYPE: PRT
<213> ORGANISM: Homo sapiens

<400> SEQUENCE: 18

```
Ser Gly Ser Ser Ser Asn Ile Gly Ser Asn Ser Leu Asn
1               5                   10

<210> SEQ ID NO 19
<211> LENGTH: 7
<212> TYPE: PRT
<213> ORGANISM: Homo sapiens

<400> SEQUENCE: 19

Ser Asn Asn Gln Arg Pro Pro
1               5

<210> SEQ ID NO 20
<211> LENGTH: 11
<212> TYPE: PRT
<213> ORGANISM: Homo sapiens

<400> SEQUENCE: 20

Ala Ala Trp Asp Asp Ser Leu Lys Gly Tyr Val
1               5                   10

<210> SEQ ID NO 21
<211> LENGTH: 120
<212> TYPE: PRT
<213> ORGANISM: Homo sapiens

<400> SEQUENCE: 21

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gln Trp Pro Asn Tyr Gly Met Asp Val Trp Gly Gln
            100                 105                 110

Gly Thr Thr Val Thr Val Ser Ser
        115                 120

<210> SEQ ID NO 22
<211> LENGTH: 110
<212> TYPE: PRT
<213> ORGANISM: Homo sapiens

<400> SEQUENCE: 22

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ser Leu Asn Trp Tyr Gln Gln Leu Pro Gly Thr Ala Pro Lys Leu Leu
        35                  40                  45

Ile Tyr Ser Asn Asn Gln Arg Pro Pro Gly Val Pro Asp Arg Phe Ser
    50                  55                  60

Gly Ser Arg Ser Gly Ser Ser Ala Ser Leu Ala Ile Ser Gly Leu Gln
```

```
                65                  70                  75                  80
Ser Gly Asp Glu Gly Asp Tyr Tyr Cys Ala Ala Trp Asp Asp Ser Leu
                    85                  90                  95

Lys Gly Tyr Val Phe Gly Thr Gly Thr Gln Leu Thr Val Leu
            100                 105                 110

<210> SEQ ID NO 23
<211> LENGTH: 360
<212> TYPE: DNA
<213> ORGANISM: Homo sapiens

<400> SEQUENCE: 23
gaggtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag catagggctat    180 gcggactctg tgaagggccg attcaccatc tccagagaca acgccaagga ctcactgtat    240
ctgcaaatga acagcctgag agccgaggac acggctgtgt attactgtgc gagagaaggg   300
cagtggccga actacggtat ggacgtctgg ggccaaggga ccacggtcac cgtctcctca    360

<210> SEQ ID NO 24
<211> LENGTH: 330
<212> TYPE: DNA
<213> ORGANISM: Homo sapiens

<400> SEQUENCE: 24
cagtctgtgt tgacgcagcc accctcagcg tctgggaccc ccgggcagag ggtcaccatc      60
tcttgttctg gaagcagctc caacatcgga agtaattctt taaactggta ccagcagctc    120
ccgggaacgg ccccccaaact cctcatctac agtaataatc agcggccccc aggggtccct   180
gaccgattct ctggctccag gtctggctcc tcggcctccc tggccatcag tgggctccag   240
tctggggatg agggtgatta ttactgtgca gcatgggatg acagcctgaa gggttatgtc    300
ttcggaactg ggacccagct caccgtttta                                                          330

<210> SEQ ID NO 25
<211> LENGTH: 13
<212> TYPE: PRT
<213> ORGANISM: Homo sapiens

<400> SEQUENCE: 25

Ser Gly Ser Ser Ser Asn Ile Gly Gly Asp Thr Val Asn
1               5                   10

<210> SEQ ID NO 26
<211> LENGTH: 11
<212> TYPE: PRT
<213> ORGANISM: Homo sapiens

<400> SEQUENCE: 26

Ala Ala Trp Asp Asp Ser Leu Asn Gly Tyr Val
1               5                   10

<210> SEQ ID NO 27
<211> LENGTH: 110
<212> TYPE: PRT
<213> ORGANISM: Homo sapiens

<400> SEQUENCE: 27

Gln Ser Val Leu Thr Gln Pro Pro Ser Ala Ser Gly Thr Pro Gly Gln
```

```
              1               5                  10                 15
           Arg Val Thr Ile Ser Cys Ser Gly Ser Ser Asn Ile Gly Gly Asp
                           20                  25                  30

Thr Val Asn Trp Tyr Gln Gln Leu Pro Gly Thr Ala Pro Lys Leu Leu
                           35                  40                  45

Ile Tyr Ser Asn Asn Gln Arg Pro Ser Gly Val Pro Asp Arg Phe Ser
                       50                  55                  60

Gly Ser Lys Ser Gly Thr Ser Ala Ser Leu Ala Ile Ser Gly Leu Arg
           65                  70                  75                  80

Ser Glu Asp Glu Ala Asp Tyr Tyr Cys Ala Ala Trp Asp Asp Ser Leu
                           85                  90                  95

Asn Gly Tyr Val Phe Gly Thr Gly Thr Lys Leu Thr Val Leu
                           100                 105                 110

<210> SEQ ID NO 28
<211> LENGTH: 330
<212> TYPE: DNA
<213> ORGANISM: Homo sapiens

<400> SEQUENCE: 28
cagtctgtgc tgactcagcc accctcagcg tctgggaccc ccgggcagag ggtcaccatc      60
tcttgttctg gaagcagctc aacatcgga ggtgatactg taaactggta ccagcagctc     120
ccaggaacgg ccccccaaact cctcatctat agtaataatc agcggccctc aggggtccct    180
gaccgattct ctggctccaa gtctggcacc tcagcctccc tggccatcag tgggctccgg    240
tctgaggatg aggctgatta ttactgtgca gcatgggatg acagcctgaa tggttatgtc    300
ttcggcactg ggaccaagct gaccgtccta                                      330

<210> SEQ ID NO 29
<211> LENGTH: 13
<212> TYPE: PRT
<213> ORGANISM: Homo sapiens

<400> SEQUENCE: 29

Ser Gly Ser Arg Ser Asn Ile Gly Ser Asn Thr Val Ser
1               5                   10

<210> SEQ ID NO 30
<211> LENGTH: 110
<212> TYPE: PRT
<213> ORGANISM: Homo sapiens

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
                20                  25                  30

Thr Val Ser Trp Tyr Gln Gln Leu Pro Gly Thr Ala Pro Lys Leu Leu
                35                  40                  45

Ile Tyr Ser Asn Asn Gln Arg Pro Ser Gly Val Pro Asp Arg Phe Ser
            50                  55                  60

Gly Ser Gln Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Leu Thr Val Leu
                100                 105                 110
```

<210> SEQ ID NO 31
<211> LENGTH: 330
<212> TYPE: DNA
<213> ORGANISM: Homo sapiens

<400> SEQUENCE: 31

```
cagtctgtgc tgactcagcc accctcagcg tctgggaccc ccgggcagag ggtcaccatc      60
tcttgttctg gaagcaggtc caacatcgga agtaatactg taagctggta ccagcaactc     120
ccaggaacgg cccccaaact cctcatctat agtaataatc agcggccctc aggggtccct     180
gaccgattct ctggctccca gtctggcacc tcagcctccc tggccatcag tggactccag     240
tctgaggatg aggctgatta ttactgtgca gcatgggatg acagcctgaa tggttatgtc     300
ttcggaactg ggaccaagct gaccgtccta                                      330
```

<210> SEQ ID NO 32
<211> LENGTH: 624
<212> TYPE: PRT
<213> ORGANISM: Homo sapiens

<400> SEQUENCE: 32

```
Ser Glu Val Gly Asn Ser Gln Ala Val Cys Pro Gly Thr Leu Asn Gly
  1               5                  10                  15

Leu Ser Val Thr Gly Asp Ala Glu Asn Gln Tyr Gln Thr Leu Tyr Lys
             20                  25                  30

Leu Tyr Glu Arg Cys Glu Val Val Met Gly Asn Leu Glu Ile Val Leu
         35                  40                  45

Thr Gly His Asn Ala Asp Leu Ser Phe Leu Gln Trp Ile Arg Glu Val
     50                  55                  60

Thr Gly Tyr Val Leu Val Ala Met Asn Glu Phe Ser Thr Leu Pro Leu
 65                  70                  75                  80

Pro Asn Leu Arg Val Val Arg Gly Thr Gln Val Tyr Asp Gly Lys Phe
                 85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
    130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln Asp Thr Asp Cys
    210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270
```

His Asn Phe Val Val Asp Gln Thr Ser Cys Val Arg Ala Cys Pro Pro
        275                 280                 285

Asp Lys Met Glu Val Asp Lys Asn Gly Leu Lys Met Cys Glu Pro Cys
    290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
                340                 345                 350

Pro Trp His Lys Ile Pro Ala Leu Asp Pro Glu Lys Leu Asn Val Phe
            355                 360                 365

Arg Thr Val Arg Glu Ile Thr Gly Tyr Leu Asn Ile Gln Ser Trp Pro
    370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
                420                 425                 430

Gly Arg Ile Tyr Ile Ser Ala Asn Arg Gln Leu Cys Tyr His His Ser
            435                 440                 445

Leu Asn Trp Thr Lys Val Leu Arg Gly Pro Thr Glu Glu Arg Leu Asp
    450                 455                 460

Ile Lys His Asn Arg Pro Arg Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
                500                 505                 510

His Cys Asn Phe Leu Asn Gly Glu Pro Arg Glu Phe Ala His Glu Ala
            515                 520                 525

Glu Cys Phe Ser Cys His Pro Glu Cys Gln Pro Met Glu Gly Thr Ala
    530                 535                 540

Thr Cys Asn Gly Ser Gly Ser Asp Thr Cys Ala Gln Cys Ala His Phe
545                 550                 555                 560

Arg Asp Gly Pro His Cys Val Ser Ser Cys Pro His Gly Val Leu Gly
                565                 570                 575

Ala Lys Gly Pro Ile Tyr Lys Tyr Pro Asp Val Gln Asn Glu Cys Arg
                580                 585                 590

Pro Cys His Glu Asn Cys Thr Gln Gly Cys Lys Gly Pro Glu Leu Gln
            595                 600                 605

Asp Cys Leu Gly Gln Thr Leu Val Leu Ile Gly Lys Thr His Leu Thr
    610                 615                 620

<210> SEQ ID NO 33
<211> LENGTH: 18
<212> TYPE: PRT
<213> ORGANISM: Homo sapiens

<400> SEQUENCE: 33

Gly Gly Cys Ser Gly Pro Gln Asp Thr Asp Cys Phe Ala Cys Arg His
1               5                   10                  15

Phe Asn

```
<210> SEQ ID NO 34
<211> LENGTH: 15
<212> TYPE: PRT
<213> ORGANISM: Homo sapiens

<400> SEQUENCE: 34

Asp Phe Leu Ile Thr Gly Leu Asn Gly Asp Pro Trp His Lys Ile
1               5                   10                  15

<210> SEQ ID NO 35
<211> LENGTH: 17
<212> TYPE: PRT
<213> ORGANISM: Homo sapiens

<400> SEQUENCE: 35

Leu Asp Phe Leu Ile Thr Gly Leu Asn Gly Asp Pro Trp His Lys Ile
1               5                   10                  15

Pro

<210> SEQ ID NO 36
<211> LENGTH: 6
<212> TYPE: PRT
<213> ORGANISM: Homo sapiens

<400> SEQUENCE: 36

Asp Pro Trp His Lys Ile
1               5
```

ANTIBODIES AGAINST HER3

FIELD OF THE INVENTION

The present invention relates to antibodies that bind to HER-3 (ErbB3).

BACKGROUND OF THE INVENTION

The human epidermal growth factor (EGF) family of receptor tyrosine kinases includes four members: EGFR (ErbB1, HER1), HER2 (c-Neu, ErbB2), HER3 (ErB3) and HER4 (ErbB4) (Hynes et. al. (1994)).

These HER receptors are predicted to consist of an extracellular ligand-binding domain, a membrane-spanning domain, a cytosolic protein tyrosine kinase (PTK) domain and a C-terminal phosphorylation domain (see, e.g., Kim et al., (1998)). Receptor activation via ligand binding leads to downstream signalling that influence cell proliferation, invasion and survival of normal cells and cancer cells.

Aberrant expression or activity of EGFR and HER2 have been correlated with many cancers including but not limited to lung, breast, ovarian, colon and bladder cancer and several targeted therapies have shown clinical efficiencies (see review of Hynes and Lane, Nature Rev., 2005).

There are two major classes of anti-HER therapeutics: ectodomain-binding antibodies (cetuximab, panitumumab and trastuzumab) and inhibitor of the tyrosine kinase domain (erlotinib, gefitinib, and lapatinib). A majority of these clinical therapies target EGFR and HER2 receptors.

However, despite their clinical success, these targeted therapies over EGFR and HER2 are limited due to acquired resistance problems. Indeed, patients that receiving these agents exhibit primary or intrinsic resistance to these inhibitors and for those who do not respond they eventually manifest secondary or acquired resistance (Kruser and Wheeler, Exp Cell Res, 2010). Moreover, these therapies are prescribed only at certain stages of malignant disease. Only 20-30% of patients with breast cancer over-expressing the HER2 receptor or demonstrating HER2 gene amplification in tumors, are eligible for treatment with Trastuzumab, reducing its therapeutic indications.

A further HER receptor, HER3 has also been described (Plowman (1990)), and it role in cancer has been explored (Horst et al. (2005); Xue et al. (2006)).

Binding of the ligand Heregulin (HRG) to HER3 receptor triggers the heterodimerization of HER3 with the others HER family receptors. Within the heterodimer, the HER3 kinase domain acts as an allosteric activator of its HER family partner (Campiglio M, et al. (1999); Karamouzis M V et al. (2007)).

The heterodimer HER2/HER3 has the strongest mitogenic activity in the HER family and is the major oncogenic signal leading to the proliferation and invasion of tumor cells in breast cancers (Citri et al. (2006); Lee-Hoeflich et al. (2008)).

Besides being over-expressed in numerous human cancers, such as breast, gastrointestinal, ovarian and pancreatic cancers, HER3 expression or signalling has been found associated with resistance to antibody-based therapies against the EGFR and HER2 (see for review Campbell et al., (2010)). In addition, it has been shown that tumors with low expression of HER2, which are not eligible for treatment with trastuzumab, often demonstrate a high expression of HER3 receptor, associated with poor prognosis (Travis et al. (1996); Naidu et al. (1998), Menendez et al. (2006)). In both cases, this HER3 programming promotes the formation of HER2/HER3 heterodimers.

The great potential of HER3 and the need to alternatives to therapy inhibiting EGFR or HER2 to face mechanisms of resistance, suggest that HER3-targeted agents, and in particular antibodies, might be used as efficient immuno-therapeutics.

Murine and chimeric anti-HER3 antibodies have been reported: U.S. Pat. No. 5,968,511, U.S. Pat. No. 5,480,968, WO03013602. Human anti-HER3 antibodies have also been reported: US2008/0124345, US2009/0291085A1.

Nevertheless the growing part of HER3 in many types of cancers and the complexity of cooperation and interdependence between the HER family and notably concerning the HER3 receptor, lead to the need of more drugs targeted this receptor as well as the complex HER2-HER3.

SUMMARY OF THE INVENTION

The present invention relates to an anti-HER3 antibody comprising a heavy chain wherein the variable domain comprises SEQ ID NO: 1 for H-CDR1, SEQ ID NO: 2 for H-CDR2 and SEQ ID NO: 3 for H-CDR3.

The present invention also relates to a pharmaceutical composition comprising said antibody and a pharmaceutically acceptable carrier.

The invention further relates to an antibody of the invention for use in the treatment of cancer.

DETAILED DESCRIPTION OF THE INVENTION

Definitions

The term "anti-HER3 antibody" refers to an antibody directed against HER3, in particular human HER3. Anti-HER3 antibody might be directed against HER3 monomer or HER3 in a heterodimer comprising HER3 selected from the group consisting of HER2-HER3, also called therein HER2-HER3 complex, EGFR-HER3 and HER4-HER3.

HER3 sequence is disclosed in uniprot under the reference number P21860. Hereinafter, the amino acids of HER3 are numbered in reference to uniprot.

In one specific embodiment, the term "anti-HER3 antibody" refers to an antibody that binds to the extracellular domain of human HER3 polypeptide as defined in SEQ ID NO: 32 (Table A).

TABLE A

| Amino acid sequence of HER3 extracellular domain 20-643 | |
|---|---|
| Amino acid sequence of human HER3 extracellular domain | SEVGNSQAVCPGILNGLSVTGDAENQYQTLYKLYERCEVVMGNLEIVLTG HNADLSFLQWIREVTGYVLVAMNEFSTLPLPNLRVVRGTQVYDGKFAIFVM LNYNTNSSHALRQLRLTQLTEILSGGVYIEKNDKLCHMDTIDWRDIVRDRDA EIVVKDNGRSCPPCHEVCKGRCWGPGSEDCQTLTKTICAPQCNGHCFGP NPNQCCHDECAGGCSGPQDTDCFACRHFNDSGACVPRCPQPLVYNKLTF QLEPNPHTKYQYGGVCVASCPHNFVVDQTSCVRACPPDKMEVDKNGLKM |

TABLE A -continued

Amino acid sequence of HER8 extracellular domain 20-643

| 20-643; P21860 uniprot) | CEPCGGLCPKACEGTGSGSRFQTVDSSNIDGFVNCTKILGNLDFLITGLNG DPWHKIPALDPEKLNVFRTVREITGYLNIQSWPPHMHNFSVFSNLTTIGGRS LYNRGFSLLIMKNLNVISLGFRSLKEISAGRIYISANRQLCYHHSLNWTKVLR GPTEERLDIKHNRPRRDCVAEGKVCDPLCSSGGCWGPGPGQCLSCRNYS RGGVCVTHCNFLNGEPREFAHEAECFSCHPECQPMEGTATCNGSGSDTC AQCAHFRDGPHCVSSCPHGVLGAKGPIYKYPDVQNECRPCHENCTQGCK GPELQDCLGQTLVLIGKTHLT (SEQ ID NO: 32) |
|---|---|

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments, including antigen-binding fragments, as well as variants (including derivatives) of antibodies and antibody fragments. In conventional antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

As used therein, residues of antibodies are numbered according to Kabat scheme.

The term "human antibody" refers to an antibody in which a substantial portion of the antibody molecule resembles, in amino acid sequence or structure, that of an antibody derived from human origin. Typically, H3A-32, H3A-76, H3A-81, H4B-05 and H4B-121 are human antibodies.

A "human antibody" may be considered more suitable in instances where it is desirable to reduce the immunogenicity of the antibody for administration to humans for therapeutic purposes.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to a polypeptide (i.e. an antibody according to the invention) or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

A "therapeutically effective amount" is intended for a minimal amount of active agent (e.g., anti-HER3 antibodies) which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

As used herein, the term "subject" denotes a mammal, such as a rodent, a feline, a canine, and a primate. Preferably a subject according to the invention is a human.

"Treatment or treating" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. Hence, the subject to be treated herein may have been diagnosed as having the disorder or may be predisposed or susceptible to the disorder.

The terms "cancer" and "cancerous" refer to or describe the physiological condition in subjects that is typically characterized by unregulated cell growth or death. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Antibodies and Polypeptides of the Invention

The inventors have cloned and characterized the variable domains of the light and heavy chains of many human anti-HER3 monoclonal antibodies (mAbs). Among these mAbs, the inventors have identified that mAbs with complementarity determining regions (CDRs), as described in table 1, were inhibitors of HER3 biological activity.

The inventors have, in particular, shown that these anti-HER3 antibodies were potent inhibitors of the formation of a heterodimer comprising HER3 selected from the group consisting of HER2-HER3 complex, EGFR-HER3 and HER4-HER3, and more particularly of the formation of HER2-HER3 complex.

The inventors have, notably, shown that the antibodies of the invention exhibit a higher binding to HER3 when HER3 is in the heterodimer HER2-HER3 compared with known anti-HER3 antibodies, for example those described in patent US2008/0124345A1 and US2009/0291085A1.

Further, the inventors have also shown that the antibodies of the invention inhibit the binding of heregulin to HER3.

TABLE 1

| H-CDR domains of anti-HER3 antibodies according to the invention: | |
|---|---|
| H-CDR1 | DYAMH (SEQ ID NO: 1) |
| H-CDR2 | ISWNSGSIGYADSVKG (SEQ ID NO: 2) |
| H-CDR3 | EGQWPNYGMDV (SEQ ID NO: 3) |

The invention relates to an anti-HER3 antibody comprising a heavy chain wherein the variable domain comprises SEQ ID NO: 1 for H-CDR1, SEQ ID NO: 2 for H-CDR2 and SEQ ID NO: 3 for H-CDR3.

Among the antibodies of the invention, five antibodies have shown particularly good results. They are named mAb H3A-32, mAb H3A-76, mAb H3A-81, mAb H4B-05 and mAb H4B-121. The VH, VL and CDR domains of these antibodies are respectively described in table 2 to 6.

TABLE 2

| VH, VL and CDR domains of mAb H3A-32: | |
|---|---|
| MAb H3A-32 Domains | |
| VH | EVQLVESGGGLVQPGGSLRLSCAASGFTFDDYAMHWVRQA PGKGLEWVSGISWNSGSIGYADSVKGRFTISRDNAKNSLYL QMNSLRAEDTAVYYCAREGQWPNYGMDVWGQGTTVTVS S (SEQ ID NO: 14) |
| VH CDR1 | DYAMH (SEQ ID NO: 1) |
| VH CDR2 | ISWNSGSIGYADSVKG (SEQ ID NO: 2) |
| VH CDR3 | EGQWPNYGMDV (SEQ ID NO: 3) |
| VL | QSVLTQPPSASGTPGQRVTISCSGSSSNIGSDPVNWYQQLPG TAPKLLIYSNNQRPSGVPDRFSGSKSGTSASLAISGLQSEDEA DYYCAAWDDSLRGYVFGTGTKLTVL (SEQ ID NO: 15) |
| VL CDR1 | SGSSSNIGSDPVN (SEQ ID NO: 11) |
| VL CDR2 | SNNQRPS (SEQ ID NO: 12) |
| VL CDR3 | AAWDDSLRGYV (SEQ ID NO: 13) |

TABLE 3

| VH, VL and CDR domains of mAb H3A-76: | |
|---|---|
| MAb H3A-76 Domains | |
| VH | EVQLVESGGGLVQPGRSLRLSCAASGFTFDDYAMHWVRQA PGKGLEWVSGISWNSGSIGYADSVKGRFTISRDNAKDSLYL QMNSLRAEDTAVYYCAREGQWPNYGMDVWGQGTTVTVS S (SEQ ID NO: 21) |
| VH CDR1 | DYAMH (SEQ ID NO: 1) |
| VH CDR2 | ISWNSGSIGYADSVKG (SEQ ID NO: 2) |
| VH CDR3 | EGQWPNYGMDV (SEQ ID NO: 3) |
| VL | QSVLTQPPSASGTPGQRVTISCSGSSSNIGSNSLNWYQQLPG TAPKLLIYSNNQRPPGVPDRFSGSRSGSSASLAISGLQSGDEG DYYCAAWDDSLKGYVFGTGTQLTVL (SEQ ID NO: 22) |
| VL CDR1 | SGSSSNIGSNSLN (SEQ ID NO: 18) |
| VL CDR2 | SNNQRPP (SEQ ID NO: 19) |
| VL CDR3 | AAWDDSLKGYV (SEQ ID NO: 20) |

TABLE 4

VH, VL and CDR domains of mAb H3A-81:

| MAb H3A-81 Domains | |
|---|---|
| VH | EVQLVESGGGLVQPGGSLRLSCAASGFTFDDYAMHWVRQAPGKGLEWVSGISWNSGSIGYADSVKGRFTISRDNAKNSLYLQMNSLRAEDTAVYYCAREGQWPNYGMDVWGQGTTVTVSS (SEQ ID NO: 14) |
| VH CDR1 | DYAMH (SEQ ID NO:1) |
| VH CDR2 | ISWNSGSIGYADSVKG (SEQ ID NO: 2) |
| VH CDR3 | EGQWPNYGMDV (SEQ ID NO: 3) |
| VL | QSVLTQPPSASGTPGQRVTISCSGSSSNIGGDTVNWYQQLPGTAPKLLIYSNNQRPSGVPDRFSGSKSGTSASLAISGLRSEDEADYYCAAWDDSLNGYVFGTGTKLTVL (SEQ ID NO: 27) |
| VL CDR1 | SGSSSNIGGDTVN (SEQ ID NO: 25) |
| VL CDR2 | SNNQRPS (SEQ ID NO: 12) |
| VL CDR3 | AAWDDSLNGYV (SEQ ID NO: 26) |

TABLE 5

VH, VL and CDR domains of mAb H4B-05:

| MAb H4B-05 Domains | |
|---|---|
| VH | EVQLVESGGGLVQPGRSLRLSCAASGFTFDDYAMHWVRQAPGKGLEWVSGISWNSGSIGYADSVKGRFTISRDNAKNSLYLQMNSLRAEDTAVYYCAREGQWPNYGMDVWGQGTTVTVSS (SEQ ID NO: 7) |
| VH CDR1 | DYAMH (SEQ ID NO: 1) |
| VH CDR2 | ISWNSGSIGYADSVKG (SEQ ID NO: 2) |
| VH CDR3 | EGQWPNYGMDV (SEQ ID NO: 3) |
| VL | QSVLTQPPSASGTPGQRVTISCSGSRSNIGSNTVSWYQQLPGTAPKLLIYSNNQRPSGVPDRFSGSQSGTSASLAISGLQSEDEADYYCAAWDDSLNGYVFGTGTKLTVL (SEQ ID NO: 30) |
| VL CDR1 | SGSRSNIGSNTVS (SEQ ID NO: 29) |
| VL CDR2 | SNNQRPS (SEQ ID NO: 12) |
| VL CDR3 | AAWDDSLNGYV (SEQ ID NO: 26) |

TABLE 6

VH, VL and CDR domains of mAb H4B-121:

| MAb H4B-121 Domains | |
|---|---|
| VH | EVQLVESGGGLVQPGRSLRLSCAASGFTFDDYAMHWVRQAPGKGLEWVSGISWNSGSIGYADSVKGRFTISRDNAKNSLYLQMNSLRAEDTAVYYCAREGQWPNYGMDVWGQGTTVTVSS (SEQ ID NO: 7) |
| VH CDR1 | DYAMH (SEQ ID NO: 1) |
| VH CDR2 | ISWNSGSIGYADSVKG (SEQ ID NO: 2) |
| VH CDR3 | EGQWPNYGMDV (SEQ ID NO: 3) |
| VL | QSVLTQPPSVSAAPGQKVTISCPGSSSNIGNNYVSWYQQLPGTAPKLLIYDNNERPSGIPDRFSGSTSGTSATLDITDLQAEDEATYYCGAWDNTLGVYVLGTGTQLTVL (SEQ ID NO: 8) |
| VL CDR1 | PGSSSNIGNNYVS (SEQ ID NO: 4) |
| VL CDR2 | DNNERPS (SEQ ID NO: 5) |
| VL CDR3 | GAWDNTLGVYV (SEQ ID NO: 6) |

Therefore, in a particular embodiment, the heavy chain variable domain has the amino acid sequence selected from the group consisting of SEQ ID NO: 7, SEQ ID NO: 14 and SEQ ID NO: 21.

In another particular embodiment, the light chain variable domain of the antibody according to the invention comprises a light chain which the variable domain comprises:

L-CDR1 selected from the group consisting of SEQ ID NO: 4, SEQ ID NO: 11, SEQ ID NO: 18, SEQ ID NO: 25 and SEQ ID NO: 29, L-CDR2 selected from the group consisting of SEQ ID NO: 5, SEQ ID NO: 12 and SEQ ID NO: 19, and L-CDR3 selected from the group consisting of SEQ ID NO: 6, SEQ ID NO: 13, SEQ ID NO: 20 and SEQ ID NO: 26.

In one embodiment, the light chain variable domain has the amino acid sequence selected from the group consisting of SEQ ID NO: 8, SEQ ID NO: 15, SEQ ID NO: 22, SEQ ID NO: 27 and SEQ ID NO: 30.

In one embodiment, said anti-HER3 antibody is selected from the group consisting of:

an antibody comprising the heavy chain variable domain having the amino acid sequence set forth as SEQ ID NO: 7, and the light chain variable domain having the amino acid sequence selected from the group consisting of SEQ ID NO: 8 and SEQ ID NO: 30, an antibody comprising the heavy chain variable domain having the amino acid sequence set forth as SEQ ID NO: 14, and the light chain variable domain having the amino acid sequence selected from the group consisting of SEQ ID NO: 15 and SEQ ID NO: 27 and an antibody comprising the heavy chain variable domain having the amino acid sequence set forth as SEQ ID NO: 21, and the light chain variable domain having the amino acid sequence selected from the group consisting of SEQ ID NO: 22.

In a more particular embodiment, said anti-HER3 antibody is a human antibody.

Said antibodies can be produced by any technique well known in the art. In particular, said antibodies are produced by techniques as hereinafter described.

The invention further provides for fragments of said antibodies which include but are not limited to Fv, Fab, F(ab')2, Fab', dsFv, scFv, sc(Fv)2 and diabodies; and multispecific antibodies formed from antibody fragments.

Antibodies and polypeptides of the invention can be used in an isolated (e.g., purified) form or contained in a vector, such as a membrane or lipid vesicle (e.g. a liposome).

Nucleic Acids, Vectors and Recombinant Host Cells

A further object of the invention relates to a nucleic acid comprising a sequence encoding at least the heavy chain of the antibody according to the invention or an antigen-binding fragment thereof.

In a particular embodiment, the invention relates to a nucleic acid sequence encoding the VH domain or the VL domain of mAb H3A-32, mAb H3A-76, mAb H3A-81, mAb H4B-05 and mAb H4B-121 as disclosed in Table 7.

TABLE 7

Nucleic acids of VH and VL domains of mAbs of to the invention

| | | |
|---|---|---|
| mAb H3A-32 | VH domain: | GAGGTGCAGCTGGTGGAGTCCGGGGGAGGCTTAGT TCAGCCTGGGGGGTCCCTGAGACTCTCCTGTGCAGC CTCTGGATTCACCTTTGATGATTATGCCATGCACTG GGTCCGGCAAGCTCCAGGGAAGGGCCTGGAGTGGG TCTCAGGTATTAGTTGGAATAGTGGTAGCATAGGCT ATGCGGACTCTGTGAAGGGCCGATTCACCATCTCCA GAGACAACGCCAAGAACTCACTGTATCTGCAAATG AACAGCCTGAGAGCCGAGGACACGGCTGTGTATTA CTGTGCGAGAGAAGGGCAGTGGCCGAACTACGGTA TGGACGTCTGGGGCCAAGGGACCACGGTCACCGTC TCCTCA (SEQ ID NO: 16) |
| | VL domain: | CAGTCTGTGCTGACTCAGCCACCCTCAGCGTCTGGG ACCCCCGGGCAGAGGGTCACCATCTCTTGTTCTGGA AGCAGCTCCAACATCGGAAGTGATCCTGTAAACTG GTACCAGCAGCTCCCAGGAACGGCCCCCAAACTCC TCATCTATAGTAATAATCAGCGGCCCTCAGGGGTCC CTGACCGATTCTCTGGCTCCAAGTCTGGCACCTCAG CCTCCCTGGCCATCAGTGGGCTCCAGTCCGAGGATG AGGCTGATTATTACTGTGCAGCATGGGATGACAGC CTGAGGGGTTATGTCTTCGGAACTGGGACCAAGCT GACCGTCCTA (SEQ ID NO: 17) |
| mAb H3A-76 | VH domain: | GAGGTGCAGCTGGTGGAGTCTGGGGGAGGCTTGGT ACAGCCTGGCAGGTCCCTGAGACTCTCCTGTGCAGC CTCTGGATTCACCTTTGATGATTATGCCATGCACTG GGTCCGGCAAGCTCCAGGGAAGGGCCTGGAGTGGG TCTCAGGTATTAGTTGGAATAGTGGTAGCATAGGCT ATGCGGACTCTGTGAAGGGCCGATTCACCATCTCCA GAGACAACGCCAAGGACTCACTGTATCTGCAAATG AACAGCCTGAGAGCCGAGGACACGGCTGTGTATTA CTGTGCGAGAGAAGGGCAGTGGCCGAACTACGGTA TGGACGTCTGGGGCCAAGGGACCACGGTCACCGTC TCCTCA (SEQ ID NO: 23) |
| | VL domain: | CAGTCTGTGTTGACGCAGCCACCCTCAGCGTCTGGG ACCCCCGGGCAGAGGGTCACCATCTCTTGTTCTGGA AGCAGCTCCAACATCGGAAGTAATTCTTTAAACTGG TACCAGCAGCTCCCGGGAACGGCCCCCAAACTCCT CATCTACAGTAATAATCAGCGGCCCCAGGGGTCC CTGACCGATTCTCTGGCTCCAGGTCTGGCTCCTCGG CCTCCCTGGCCATCAGTGGGCTCCAGTCTGGGGATG AGGGTGATTATTACTGTGCAGCATGGGATGACAGC CTGAAGGGTTATGTCTTCGGAACTGGGACCCAGCTC ACCGTTTTA (SEQ ID NO: 24) |
| mAb H3A-81 | VH domain: | GAGGTGCAGCTGGTGGAGTCCGGGGGAGGCTTAGT TCAGCCTGGGGGGTCCCTGAGACTCTCCTGTGCAGC CTCTGGATTCACCTTTGATGATTATGCCATGCACTG GGTCCGGCAAGCTCCAGGGAAGGGCCTGGAGTGGG TCTCAGGTATTAGTTGGAATAGTGGTAGCATAGGCT ATGCGGACTCTGTGAAGGGCCGATTCACCATCTCCA GAGACAACGCCAAGAACTCACTGTATCTGCAAATG AACAGCCTGAGAGCCGAGGACACGGCTGTGTATTA CTGTGCGAGAGAAGGGCAGTGGCCGAACTACGGTA TGGACGTCTGGGGCCAAGGGACCACGGTCACCGTC TCCTCA (SEQ ID NO: 16) |
| | VL domain: | CAGTCTGTGCTGACTCAGCCACCCTCAGCGTCTGGG ACCCCCGGGCAGAGGGTCACCATCTCTTGTTCTGGA AGCAGCTCCAACATCGGAGGTGATACTGTAAACTG GTACCAGCAGCTCCCAGGAACGGCCCCCAAACTCC TCATCTATAGTAATAATCAGCGGCCCTCAGGGGTCC CTGACCGATTCTCTGGCTCCAAGTCTGGCACCTCAG |

TABLE 7 -continued

Nucleic acids of VH and VL domains of mAbs of to the invention

|  |  |  |
|---|---|---|
|  |  | CCTCCCTGGCCATCAGTGGGCTCCGGTCTGAGGATG<br>AGGCTGATTATTACTGTGCAGCATGGGATGACAGC<br>CTGAATGGTTATGTCTTCGGCACTGGGACCAAGCTG<br>ACCGTCCTA (SEQ ID NO: 28) |
| mAb H4B-05 | VH domain: | GAGGTGCAGCTGGTGGAGTCTGGGGGAGGCTTGGT<br>ACAGCCTGGCAGGTCCCTGAGACTCTCCTGTGCAGC<br>CTCTGGATTCACCTTTGATGATTATGCCATGCACTG<br>GGTCCGGCAAGCTCCAGGGAAGGGCCTGGAGTGGG<br>TCTCAGGTATTAGTTGGAATAGTGGTAGCATAGGCT<br>ATGCGGACTCTGTGAAGGGCCGATTCACCATCTCCA<br>GAGACAACGCCAAGAACTCACTGTATCTGCAAATG<br>AACAGCCTGAGAGCCGAGGACACGGCTGTGTATTA<br>CTGTGCGAGAGAAGGGCAGTGGCCGAACTACGGTA<br>TGGACGTCTGGGGCCAAGGGACCACGGTCACCGTC<br>TCCTCA (SEQ ID NO: 9) |
|  | VL domain: | CAGTCTGTGCTGACTCAGCCACCCTCAGCGTCTGGG<br>ACCCCCGGGCAGAGGGTCACCATCTCTTGTTCTGGA<br>AGCAGGTCCAACATCGGAAGTAATACTGTAAGCTG<br>GTACCAGCAACTCCCAGGAACGGCCCCCAAACTCC<br>TCATCTATAGTAATAATCAGCGGCCCTCAGGGGTCC<br>CTGACCGATTCTCTGGCTCCCAGTCTGGCACCTCAG<br>CCTCCCTGGCCATCAGTGGACTCCAGTCTGAGGATG<br>AGGCTGATTATTACTGTGCAGCATGGGATGACAGC<br>CTGAATGGTTATGTCTTCGGAACTGGGACCAAGCTG<br>ACCGTCCTA (SEQ ID NO: 31) |
| mAb H4B-121 | VH domain: | GAGGTGCAGCTGGTGGAGTCTGGGGGAGGCTTGGT<br>ACAGCCTGGCAGGTCCCTGAGACTCTCCTGTGCAGC<br>CTCTGGATTCACCTTTGATGATTATGCCATGCACTG<br>GGTCCGGCAAGCTCCAGGGAAGGGCCTGGAGTGGG<br>TCTCAGGTATTAGTTGGAATAGTGGTAGCATAGGCT<br>ATGCGGACTCTGTGAAGGGCCGATTCACCATCTCCA<br>GAGACAACGCCAAGAACTCACTGTATCTGCAAATG<br>AACAGCCTGAGAGCCGAGGACACGGCTGTGTATTA<br>CTGTGCGAGAGAAGGGCAGTGGCCGAACTACGGTA<br>TGGACGTCTGGGGCCAAGGGACCACGGTCACCGTC<br>TCCTCA (SEQ ID NO: 9) |
|  | VL domain: | CAGTCTGTGTTGACGCAGCCGCCCTCAGTGTCTGCG<br>GCCCCAGGGCAGAAGGTCACCATCTCCTGCCCTGG<br>AAGCAGCTCCAACATTGGGAATAATTATGTATCCTG<br>GTACCAGCAGCTCCCAGGGACAGCCCCCAAACTCC<br>TCATTTATGACAATAATGAGCGACCCTCAGGGATTC<br>CTGACCGATTCTCTGGCTCCACGTCTGGCACGTCAG<br>CCACCCTGGACATCACCGACCTCCAGGCTGAGGAC<br>GAGGCCACTTATTATTGCGGTGCCTGGGATAACACC<br>CTGGGTGTTTACGTCCTCGGAACTGGGACCCAGCTC<br>ACCGTTTTA (SEQ ID NO: 10) |

TABLE 8

Summary of SEQ ID NO of mAbs

|  | mAb H3A-32 | mAb H3A-76 | mAb H3A-81 | mAb H4B-05 | mAb H4B-121 |
|---|---|---|---|---|---|
| VH domain | 14 | 21 | 14 | 7 | 7 |
| Nucleic acid of VH domain | 16 | 23 | 16 | 9 | 9 |
| VL domain | 15 | 22 | 27 | 30 | 8 |
| Nucleic acid of VL domain | 17 | 24 | 28 | 31 | 10 |
| H-CDR1 | 1 | 1 | 1 | 1 | 1 |
| H-CDR2 | 2 | 2 | 2 | 2 | 2 |
| H-CDR3 | 3 | 3 | 3 | 3 | 3 |
| L-CDR1 | 11 | 18 | 25 | 29 | 4 |
| L-CDR2 | 12 | 19 | 12 | 12 | 5 |
| L-CDR3 | 13 | 20 | 26 | 26 | 6 |

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a host cell comprising a nucleic acid or a vector according to the invention.

Typically the host a cell has been transfected, infected or transformed by a nucleic acid or a vector according to the invention The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the invention in a suitable expression system. The term "expression system" means a host cell and compatible vector under suitable conditions, e.g. for the expression of a protein encoded by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

Methods of Producing Antibodies of the Invention

Antibodies of the invention may be produced by any technique known in the art, such as, without limitation, any chemical, biological, genetic or enzymatic technique, either alone or in combination.

Knowing the amino acid sequence of the desired antibody, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In particular, the invention further relates to a method of producing an antibody of the invention, which method comprises the steps consisting of: (i) culturing a transformed host cell according to the invention under conditions suitable to allow expression of said antibody; and (ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

The Fab of the present invention can be obtained by treating an antibody which specifically reacts with HER3 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody of the invention with a protease, pepsin. Also, the F(ab')2 can be produced by binding Fab' described below via a thioether bond or a disulfide bond.

The Fab' of the present invention can be obtained treating F(ab')2 of the invention with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv.

Homologous Antibodies

In yet another embodiment, an antibody of the invention has variable region heavy and light chain nucleotide sequences, or variable region heavy and light chain amino acid sequences that are homologous to the amino acid and nucleotide sequences of the antibodies described herein, and wherein the antibodies retain the desired functional properties of the anti-HER3 antibodies of the invention.

For example, the invention provides an antibody (or a functional protein comprising an antigen binding portion thereof) comprising a heavy chain wherein the variable domain comprises:

a H-CDR1 having at least 90% or 95% identity with sequence set forth as SEQ ID NO: 1, a H-CDR2 having at least 90% or 95% identity with sequence set forth as SEQ ID NO: 2, a H-CDR3 having at least 90% or 95% identity with sequence set forth as SEQ ID NO: 3, and that specifically binds to HER3 and/or HER2-HER3 complex with substantially the same affinity as an antibody comprising a heavy chain wherein the variable domain comprises SEQ ID NO: 1 for H-CDR1, SEQ ID NO: 2 for H-CDR2 and SEQ ID NO: 3 for H-CDR3, and more preferably with substantially the same affinity as one of the following antibodies: mAb H3A-32, mAb H3A-76, mAb H3A-81, mAb H4B-05 and mAb H4B-121, as described above.

Binding affinity can be measured using standard assays known in the art, such as, for example, Biacore analysis.

In one embodiment, the invention relates to homologous antibodies that bind to human HER3 and/or HER3/HER2 complex with a $K_D$ of 10 µM or less, 1 µM or 100 nM or less. As used herein, the term $K_D$ is intended to refer to the dissociation constant, which is obtained from the ratio of Kd to Ka (i.e. Kd/Ka) and is expressed as a molar concentration (M). $K_D$ values for antibodies can be determined using methods well established in the Art. One method for determining the $K_D$ of an antibody is by using surface Plasmon resonance, or using a biosensor system such as a Biacore® system.

In some specific embodiments, the antibodies of the invention have advantageously HER3 inhibiting or neutralizing activity.

As used herein, an antibody that inhibits HER3 biological activity is an antibody that inhibits the formation of heterodimer comprising HER3, in particular HER2-HER3 complex, as measured for example in T-FRET assay.

In a further example, the invention provides an antibody (or a functional protein comprising an antigen binding portion thereof) comprising a heavy chain variable region and a light chain variable region, wherein: the heavy chain variable region comprises an amino acid sequence that is at least 80%, at least 90% or at least 95% identical to an amino acid sequence selected from the group consisting of SEQ ID NO:7, SEQ ID NO: 14 and SEQ ID NO:21; the light chain variable region comprises an amino acid sequence that is at least 80%, at least 90% or at least 95% identical to an amino acid sequence selected from the group consisting of SEQ ID NO: 8, SEQ ID NO: 15, SEQ ID NO: 22, SEQ ID NO: 27 and SEQ ID NO:30; the antibody specifically binds to HER3 and/or HER2-HER3 complex with substantially the same affinity as an antibody comprising a heavy chain wherein the variable domain comprises SEQ ID NO: 1 for H-CDR1, SEQ ID NO: 2 for H-CDR2 and SEQ ID NO: 3 for H-CDR3, and more preferably with substantially the same affinity as one of the following antibodies: mAb H3A-32, mAb H3A-76, mAb H3A-81, mAb H4B-05 and mAb H4B-121, as described above.

In a further example, the invention provides an antibody, (or a functional protein comprising an antigen binding portion thereof) comprising a heavy chain variable region and a light chain variable region, wherein: the heavy chain variable region is encoded by a nucleotide sequence that is at least 80%, at least 90% or at least 95% identical to nucleotide sequence selected from the group consisting of SEQ ID NO:9, SEQ ID NO: 16 and SEQ ID NO:23; the light chain variable region is encoded by a nucleotide sequence that is at least 80%, at least 90% or at least 95% identical to a nucleotide sequence selected from the group consisting of SEQ ID NO:10, SEQ ID NO: 17, SEQ ID NO: 24, SEQ ID NO: 28 and SEQ ID NO:31; the antibody specifically binds to HER3 and/or HER2-HER3 complex with substantially the same affinity as an antibody comprising a heavy chain wherein the variable domain comprises SEQ ID NO: 1 for H-CDR1, SEQ ID NO: 2 for H-CDR2 and SEQ ID NO: 3 for H-CDR3, and more preferably with substantially the same affinity as one of the following antibodies: mAb H3A-32, mAb H3A-76, mAb H3A-81, mAb H4B-05 and mAb H4B-121, as described above.

The antibody according to the invention also encompasses antibody which specifically binds to HER3 and/or HER2-HER3 complex with substantially the same affinity as an antibody comprising a heavy chain wherein the variable domain comprises SEQ ID NO: 1 for H-CDR1, SEQ ID NO: 2 for H-CDR2 and SEQ ID NO: 3 for H-CDR3, and more preferably with substantially the same affinity as one of the following antibodies: mAb H3A-32, mAb H3A-76, mAb H3A-81, mAb H4B-05 and mAb H4B-121, as described above, and wherein 1, 2 or 3 amino acids have been substituted in either H-CDR1, H-CDR2 or H-CDR3 comparing to SEQ ID NO: 1, SEQ ID NO: 2 and SEQ ID NO: 3, respectively.

In other embodiments, the VH and/or VL amino acid sequences may be identical except an amino acid substitution in no more than 1, 2, 3, 4 or 5 amino acid position. An antibody having VH and VL regions having high (i.e., 90% or greater) identity to the VH and VL regions of SEQ ID NO:7, SEQ ID NO: 14 or SEQ ID NO:21, and SEQ ID NO:8, SEQ ID NO: 15, SEQ ID NO: 22, SEQ ID NO: 27 or SEQ ID NO:30 respectively, can be obtained by mutagenesis (e.g., site-directed or PCR-mediated mutagenesis) of nucleic acid molecules encoding SEQ ID NO:9, SEQ ID NO: 16 or SEQ ID NO:23 and SEQ ID NO:10, SEQ ID NO: 17, SEQ ID NO: 24, SEQ ID NO: 28 and SEQ ID NO:31 respectively, followed by testing of the encoded altered antibody for retained function (i.e., the functions set forth above) using the functional assays described herein.

As used herein, the percent identity between the two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller (Comput. Appl. Biosci., 4:1 1-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. MoI, Biol. 48:444-453, 1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the anti-HER3 antibodies of the invention. Accordingly, the invention provides an isolated recombinant antibody, or a functional protein comprising an antigen binding portion thereof, consisting of a heavy chain variable region comprising H-CDR1, H-CDR2, and H-CDR3 sequences and a light chain variable region comprising L-CDR1, L-CDR2, and L-CDR3 sequences, wherein:

H-CDR1 amino acid sequence is set forth as SEQ ID NO:1 and conservative modifications thereof; H-CDR2 amino acid sequences is set forth as SEQ ID NO: 2 and conservative modifications thereof; the H-CDR3 amino acid sequences is set forth SEQ ID NO: 3, and conservative modifications thereof;

L-CDR1 amino acid sequences are selected from the group consisting of SEQ ID NO:4, SEQ ID NO:11, SEQ ID NO:18, SEQ ID NO:25 and SEQ ID NO:29, and conservative modifications thereof;

L-CDR2 amino acid sequences are selected from the group consisting of SEQ ID NO:5, SEQ ID NO:12 and SEQ ID NO:19 and conservative modifications thereof;

L-CDR3 amino acid sequences are selected from the group consisting of SEQ ID NO:6, SEQ ID NO:13, SEQ ID NO:20 and SEQ ID NO:26;

the antibody specifically binds to HER3 and/or HER2-HER3 complex with substantially the same affinity as an antibody comprising a heavy chain with CDRs as follows SEQ ID NO: 1 for H-CDR1, SEQ ID NO: 2 for H-CDR2 and SEQ ID NO: 3 for H-CDR3, and more preferably with substantially the same affinity as one of the following antibodies: mAb H3A-32, mAb H3A-76, mAb H3A-81, mAb H4B-05 and mAb H4B-121, as described above.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Antibodies that Bind to the Same Epitope as Anti-HER3 Antibodies of the Invention In another embodiment, the invention provides an antibody that binds to the same epitope as do the various specific anti-HER3 antibodies of the invention described herein, and more preferably with substantially the same affinity as one of the following antibodies: mAb H3A-32, mAb H3A-76, mAb H3A-81, mAb H4B-05 and mAb H4B-121, as described above.

All the antibodies described in the Examples that are capable of specifically binding HER3 extracellular domain of HER3 bind the same epitopes with high affinity, said epitope being comprised between amino acids 20 to 643 of HER3 (SEQ ID NO: 32), preferably epitope being comprised between amino acids 214 to 231 of HER3 (SEQ ID NO: 33) and/or amino acids 343 to 357 (SEQ ID NO: 34), preferably epitope being comprised between amino acids 342 to 357 of HER3 (SEQ ID NO: 35)

In a preferred embodiment, the anti-HER3 antibody of the invention binds to the epitope being comprised between amino acids 352 to 357 of HER3 (SEQ ID NO: 36).

The epitope being comprised between amino acids 352 to 357 of HER3 (SEQ ID NO: 36) is not in the binding site of heregulin to HER3.

TABLE 9

| Amino acid sequences wherein are comprised the epitopes | |
|---|---|
| Amino acid sequence of human HER3 extracellular domain 20-643; P21860 uniprot) | SEVGNSQAVCPGILNGLSVTGDAENQYQTLYKLYERCEVVMGNLEIVLTG HNADLSFLQWIREVTGYVLVAMNEFSTLPLPNLRVVRGTQVYDGKFAIFVM LNYNTNSSHALRQLRLTQLTEILSGGVYIEKNDKLCHMDTIDWRDIVRDRDA EIVVKDNGRSCPPCHEVCKGRCWGPGSEDCQTLTKTICAPQCNGHCFGP NPNQCCHDECAGGCSGPQDTDCFACRHFNDSGACVPRCPQPLVYNKLTF QLEPNPHTKYQYGGVCVASCPHNFVVDQTSCVRACPPDKMEVDKNGLKM CEPCGGLCPKACEGTGSGSRFQTVDSSNIDGFVNCTKILGNLDFLITGLNG DPWHKIPALDPEKLNVFRTVREITGYLNIQSWPPHMHNFSVFSNLTTIGGRS LYNRGFSLLIMKNLNVISLGFRSLKEISAGRIYISANRQLCYHHSLNWTKVLR GPTEERLDIKHNRPRRDCVAEGKVCDPLCSSGGCWGPGPGQCLSCRNYS RGGVCVTHCNFLNGEPREFAHEAECFSCHPECQPMEGTATCNGSGSDTC AQCAHFRDGPHCVSSCPHGVLGAKGPIYKYPDVQNECRPCHENCTQGCK GPELQDCLGQTLVLIGKTHLT (SEQ ID NO: 32) |
| Amino acid sequence of human HERS 214-231; P21860 uniprot) | GGCSGPQDTDCFACRHFN (SEQ ID NO: 33) |

TABLE 9 -continued

Amino acid sequences wherein are comprised the epitopes

| | |
|---|---|
| Amino acid sequence of human HER3 343-357; P21860 uniprot) | DFLITGLNGDPWHKI (SEQ ID NO: 34) |
| Amino acid sequence of human HER3 342-358; P21860 uniprot) | LDFLITGLNGDPWHKIP (SEQ ID NO: 35) |
| Amino acid sequence of human HER3 352-357; P21860 uniprot) | DPWHKI (SEQ ID NO: 36) |

Additional antibodies can therefore be identified based on their ability to cross-compete (e.g., to competitively inhibit the binding of, in a statistically significant manner) with other antibodies of the invention in standard HER3 binding assays. The ability of a test antibody to inhibit the binding of antibodies of the present invention to human HER3 demonstrates that the test antibody can compete with that antibody for binding to human HER3; such an antibody may, according to non-limiting theory, bind to the same or a related (e.g., a structurally similar or spatially proximal) epitope on human HER3 as the antibody with which it competes. Thus, another aspect of the invention provides antibodies that bind to the same antigen as, and compete with, the antibodies disclosed herein by sequence. In a certain embodiment, the antibody that binds to the same epitope on human HER3 as the antibodies of the present invention is a human recombinant antibody. Such human recombinant antibodies can be prepared and isolated as described in the Examples.

Framework or Fc Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by ldusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcγRI, FcγRII, FcγRIII and FcRn have been mapped and variants with improved binding have been described (see Shields, R. L. et al., 2001 J. Biol. Chen. 276:6591-6604, WO2010106180).

In still another embodiment, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in one embodiment, the antibodies of the invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Eureka Therapeutics further describes genetically engineered CHO mammalian cells capable of producing antibodies with altered mammalian glycosylation pattern devoid of fucosyl residues (http://www.eurekainc.com/a&boutus/companyoverview.html). Alternatively, the antibodies of the invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094.

Another possibility is a fusion of at least the antigen-binding region of the antibody of the invention to proteins capable of binding to serum proteins, such human serum albumin to increase half life of the resulting molecule. Such approach is for example described in Nygren et al., EP 0 486 525.

Therapeutic Uses of the Antibodies of the Invention

A further object of the invention provides anti-HER3 antibody for use as a drug.

The invention relates to the use of an anti-HER3 antibody according to the invention as a drug.

As previously discussed, HER3 is known to play a key role in cancer.

Therefore, a further aspect of the invention provides methods and pharmaceutical compositions for the treatment of cancer or other related disorders where HER2-HER3 complex and/or HER3 has been shown to be a therapeutic target.

The invention thus relates to an antibody of the invention for use in the treatment of cancer.

The invention also relates to the use of an anti-HER3 antibody according to the invention in the preparation of a drug useful for the treatment of cancer. The invention also relates to a method for treating cancer which comprises the step of administering to a subject in need thereof an antibody of the invention.

The invention also relates to pharmaceutical composition comprising antibodies of the invention and a pharmaceutically acceptable carrier.

Therefore, antibodies of the invention may optionally be combined with sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention also provides kits comprising at least one antibody of the invention. Kits containing antibodies of the invention find use therapeutic assays.

The invention will be further illustrated by the following figures and examples. However, these examples and figures should not be interpreted in any way as limiting the scope of the present invention.

FIGURES

FIG. 1 shows the results of specificity binding Phage-ELISA for several antibodies according to the invention.

FIG. 2 shows an example of the competitive ELISA results. The competitive ELISA was performed by a competition for binding to HER3 (EbB3) between the phage-scFv H3A-81 versus each other human Fabs. The residual binding of the phage-scFv-H3A-81 at a concentration of 2 µg/ml of Fabs used as competitor was assigned in percentage. An irrelevant Fab (clone H3A-02) was used as negative control. The Fab H3A-81 was used as positive control (competition with himself: phage-scFv-H3A-81 versus Fab-H3A-81).

FIGS. 7A-F show flow cytometry specific binding profile of purified human IgG H3A-81, H3A-32, H4B-05, H3A-76 and H4B-121 to wt (A), EGFR (B), HER2 (C), EGFR/HER4 (D), HER3 (E) and HER2/HER3 complex (F) transfected NIH 3T3 cells. T⁻ is the negative control clone H3A-02.

Figure 8:
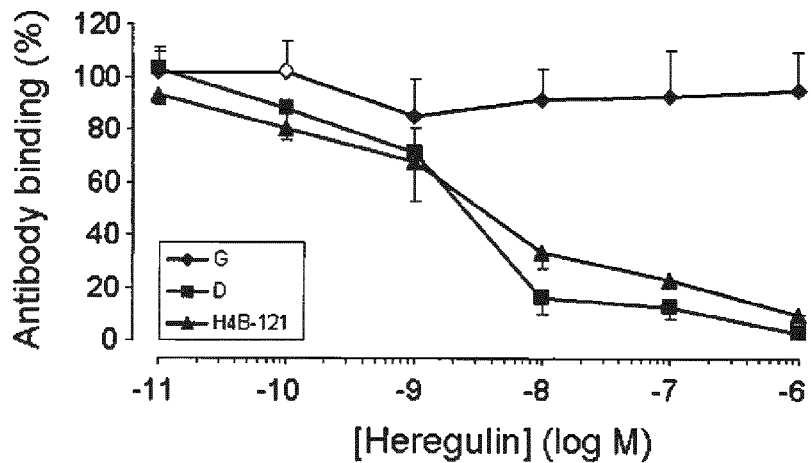

FIG. 8 shows the FACS competition experiment between HER3-specific antibody H4B-121, two others anti-HER3 (D and G) used as control antibodies, and heregulin on SKBR3 cells.

Figure 9:
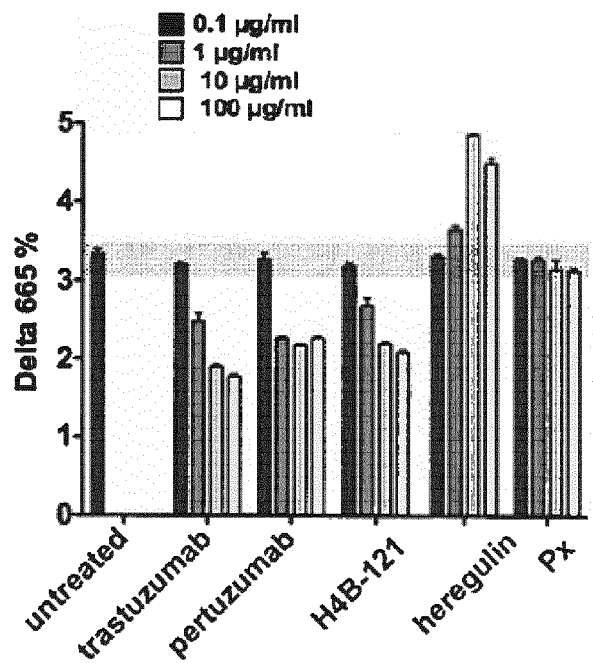

FIG. 9 shows the results of the TR-FRET assay for HER2-HER3 heterodimerization analysis in transfected NIH-3T3 cells. The anti-HER2 antibodies trastuzumab and pertuzumab were used as positive control. The irrelevant mAb Px was the negative control.

Figure 10:
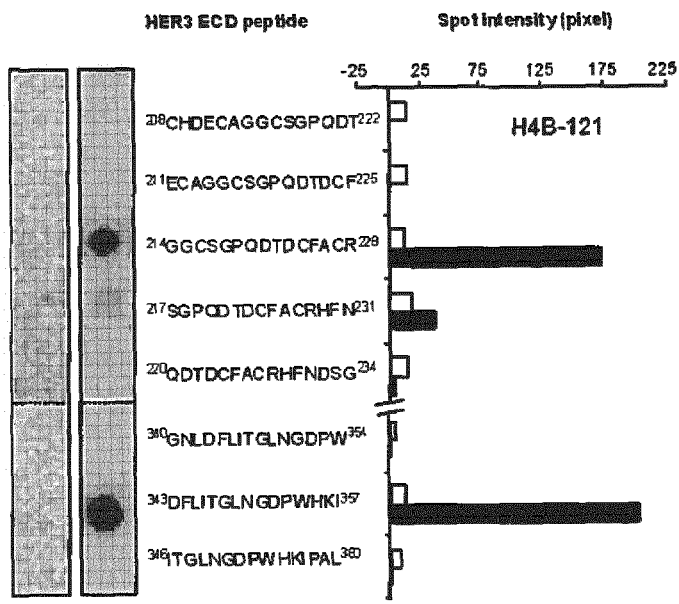

FIG. 10 shows the epitope analysis recognized by the antibody H4B-121. Spot binding was measured by pixel quantification of H4B-121 binding to HER3 (peptides 5imageJ software).

Figure 11:
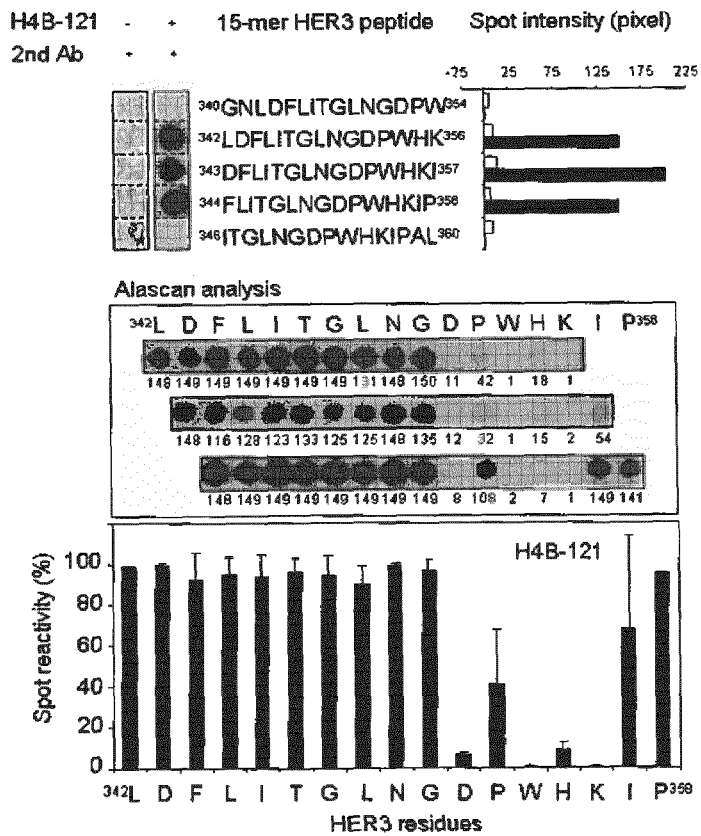
Figure 12:
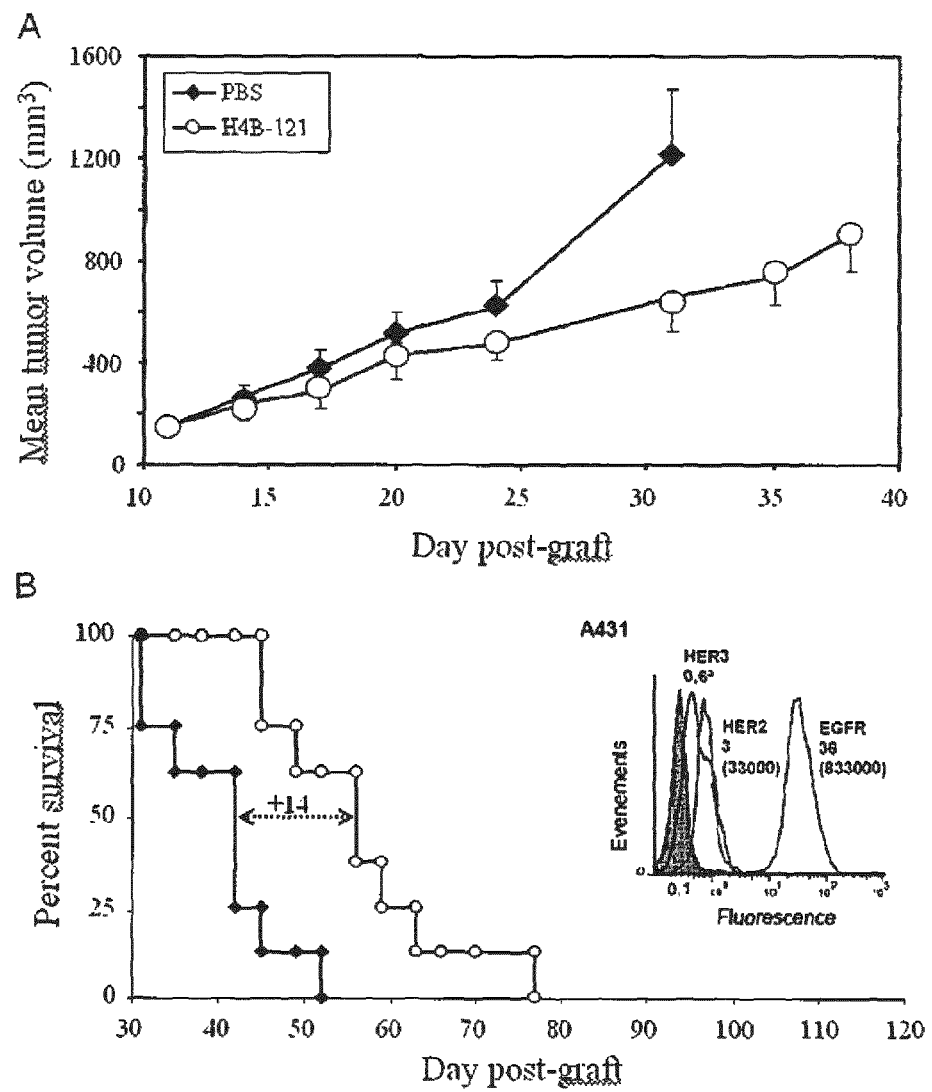

FIG. 11 identifies the Spot-Contributing Residues (SCR) on the HER3 receptor which interact with H4B-121 antibody FIGS. 12A-B show the inhibition of tumor progression by the antibody H4B-121 in nude mice xenografted with epidermoid A431 cancer cells (A), and the corresponding Kaplan-Meier survival curve (B). The relative expression of the EGFR, HER2 and HER3 receptors at the surface of A431 cells are also indicated.

Figure 13:
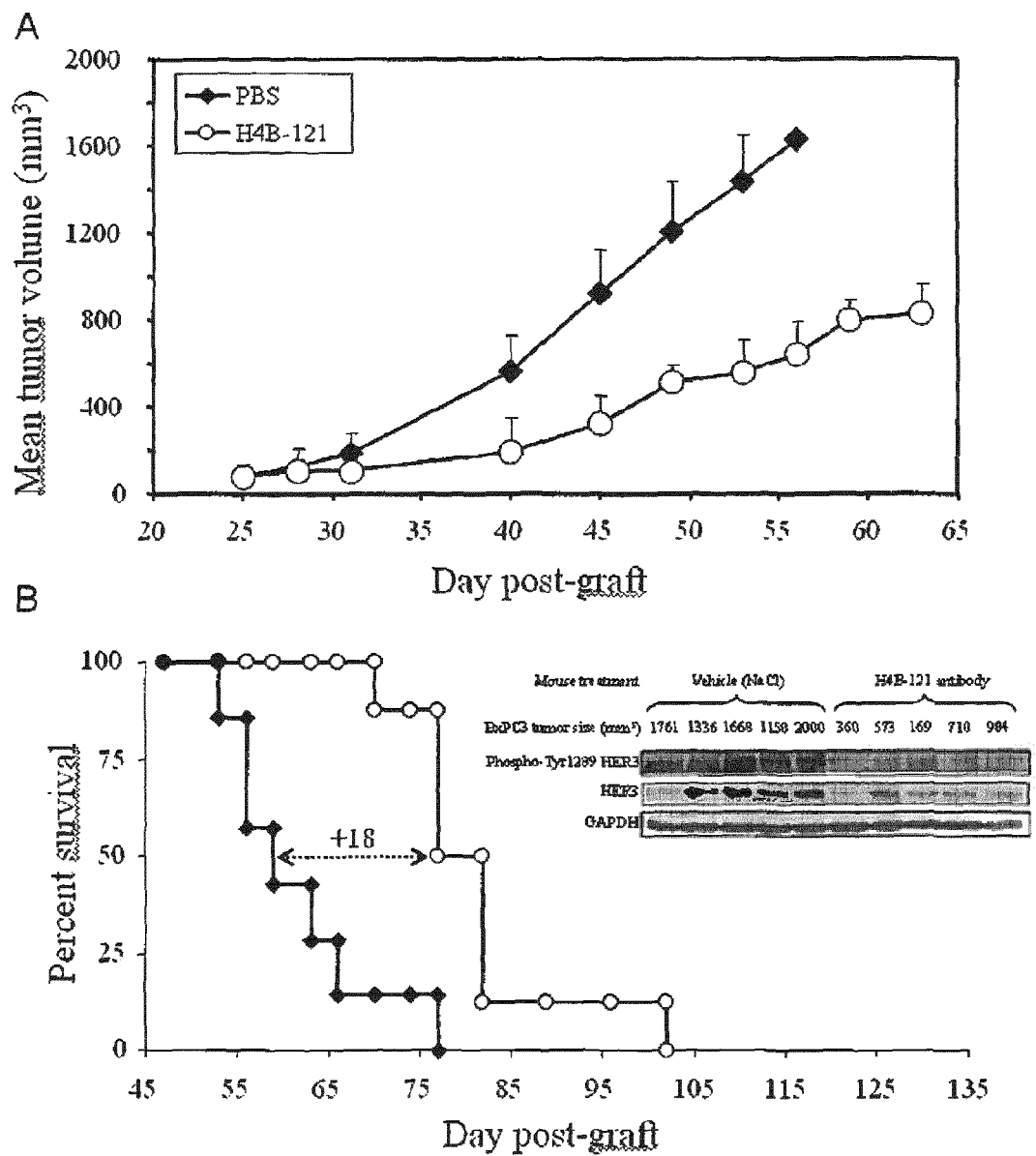

FIG. 13 show the inhibition of tumor progression by the antibody H4B-121 in nude mice xenografted with pancreatic BxPC3 cancer cells (A) and the corresponding Kaplan-Meier survival curve (B). Inside blot in FIG. 13B shows the phosphorylation level of the HER3 receptor in extracted BxPC3 xenografts from vehicle- or H4B-121-treated mice.

Figure 14:
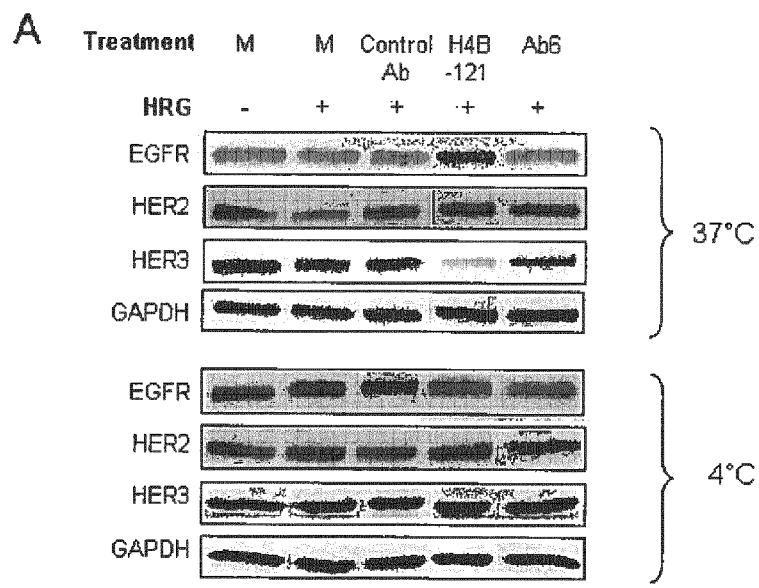
Figure 14:
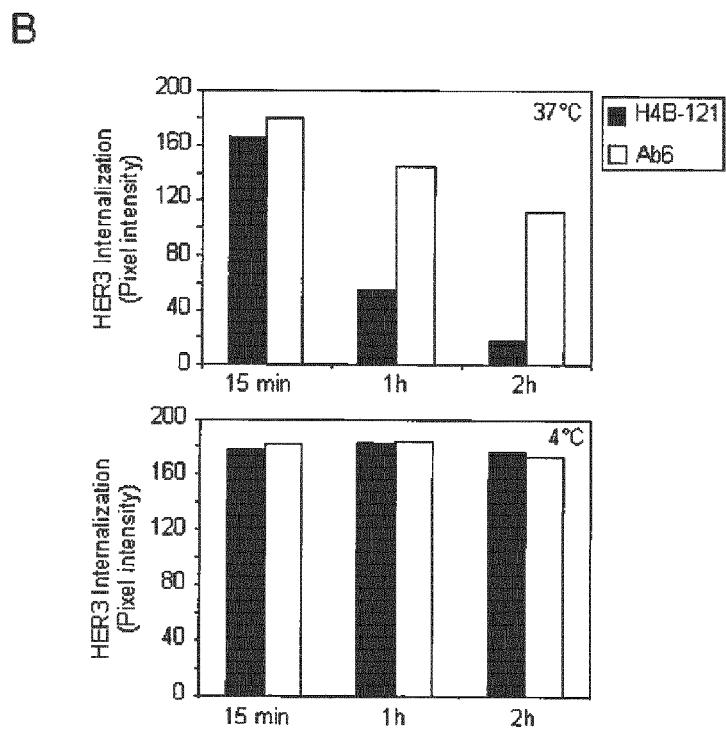

FIG. 14A shows H4B-121-induced inhibition of HER3 internalization in BxPC3 pancreatic carcinoma by western blot and FIG. 14B quantifies time-dependent antibody-induced HER3 internalization.

EXAMPLE

Specificity Phage ELISA

A human scFv phage library was screened against HER3-Fc protein (R&D Systems) to select anti-HER3 antibodies. $10^5$ clones were selected.

Figure 1:
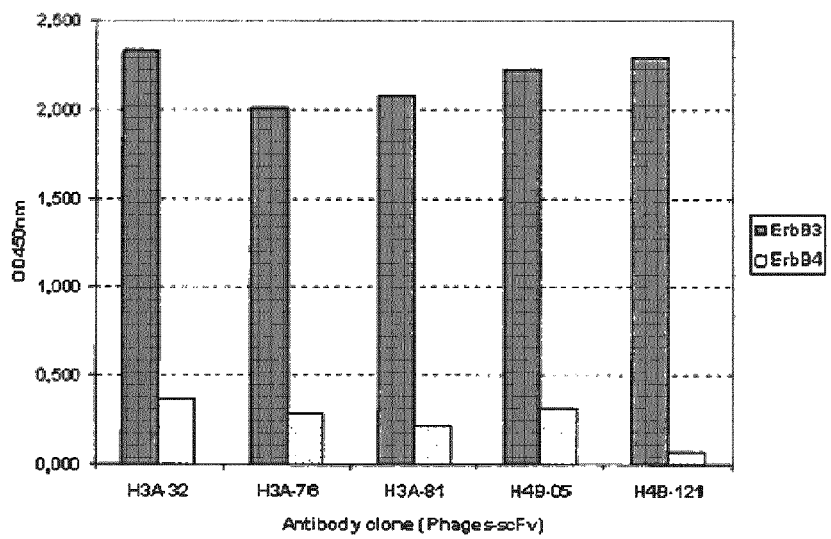

The scFv binders were assessed by phage-ELISA assay to determine the specificity for HER3 over other HER receptor (HER4 for example here). Phages-scFv expression and phage-ELISA assay were similar as described above. Each Phages-scFv supernatants were added to the microtiter plate wells previously coated with human HER3-Fc, human HER4-Fc (recombinant human extracellular domain ErbB3/HER3 or ErbB4/HER4 Fc chimera, R&D Systems) or Bovine serum Albumin. HER4-Fc and BSA were used as negative controls. As shown in FIG. 1, several Phages-scFv that exhibited specific binding for HER3 over HER4 have been isolated from the human scFv library.

Sequences Analysis of the scFv Binders

The DNA sequence of the scFv binders was determined. Analysis of the scFv DNA sequences has showed that 57/105 clones were unique. Moreover, this genetic diversity analysis after the selection shows a preferential enrichment of the clone H3A-76 (34/105). Four other clones H3A-32 (2/105), H3A-81, H4B-05 (2/105) and H4B-121 share the three CDR-H (SEQ ID NO:1 for H-CDR1; SEQ ID NO: 2 for H-CDR2; SEQ ID NO: 3 for H-CDR3,) as the H3A-76 clone.

The sequence of the amino acid sequences of the variable heavy (VH) and light chain (VL) regions for the clones H3A-32 H3A-76, H3A-81, H4B-05 and H4B-121 is set forth in Tables 2 to 6. Clones H3A-32 and H3A-81 have identical entire VH domain and H4B-05 and H4B-121 have also a same VH domain. Tables 2 to 6 show the amino acid sequences of the CDR of the variable heavy (CDR-H) and light chain (CDR-L) regions.

Construction of Human Anti-HER3 Fab Fragments, Production and Binding Characterization Conversion in Fab Format The clones H3A-32, H3A-76, H3A-81, H4B-05, H4B-121 were converted in the Fab format. The VH and VL regions were subcloned in a bicistronic bacteria expression vector that permit the periplasmic expression of Fab fragment with a V5 tag for detection and a C-terminal 6×His tag for purification. pMG92 was used for clones with a kappa light chain and pMG94 were used for clones with a lambda light chain. VH domains were cloned using NcoI/XhoI restriction site and VL domains were cloned using BamHI/SalI restriction site. Expression of Fabs was performed in HB2151 $E$ $coli$ strain with IPTG induction (0.5 mM) during 16 hours at 20° C. Cell cultures were collected and periplasmic fractions were prepared by standard protocols. Purification was done using Ni-NTA resin (Qiagen). Expression of Fabs from these systems yields from 50-200 μg depending on the Fab.

Fab Binding

The purified human Fabs at various concentrations were incubated for 2 hours at 37° C. in coated wells at 250 ng HER3-Fc (or HER4-Fc). The bound Fabs were detected by using HRP-labeled anti-V5 antibody (Invitrogen). Revelation was done at 450 nm in the presence of TMB (Sigma). The Fabs were tested simultaneously for binding on HER3-Fc, HER4-Fc and on Bovine serum Albumin as control. All the Fabs clones described above exhibited high specific binding on HER3 with no cross-reactivity over HER4.

Competitive Binding of the Human Anti-HER3 Antibodies

The HER3 epitope bound by each antibody of the invention can be determined by competitive binding analysis. The aim was to group the anti-HER3 antibodies based on their ability to block binding of each others. The competition for binding to HER3 of each anti-HER3 between them was compared with the competition by an irrelevant antibody used as negative control and with the competition by the antibody clone evaluated to itself as a positive control. This competitive binding assay can be done in different format of the anti-HER3 antibody. As described in this example, the competitive experiments were done in the phage-scFv format at a defined concentration versus Fab at various dilutions.

Briefly, $10^{10}$ of PEG purified phage-scFv were mixed with various concentration of purified Fabs (from $1\times10^{-7}$ M to $2\times10^{-10}$ M). The mixture was added to the microtiter plate 96 wells pre-coated with HER3-Fc at 50 ng and blocked with Bovine serum Albumin. The plates were incubated 2 hours at 37° C., and then washed three times. The residual bound phages-scFv were detected by adding HRP conjugate anti-M13 antibody (GE Healthcare) during 2 hours at 37° C., and were revealed at 450 nm in the presence of TMB (Sigma).

Figure 2:
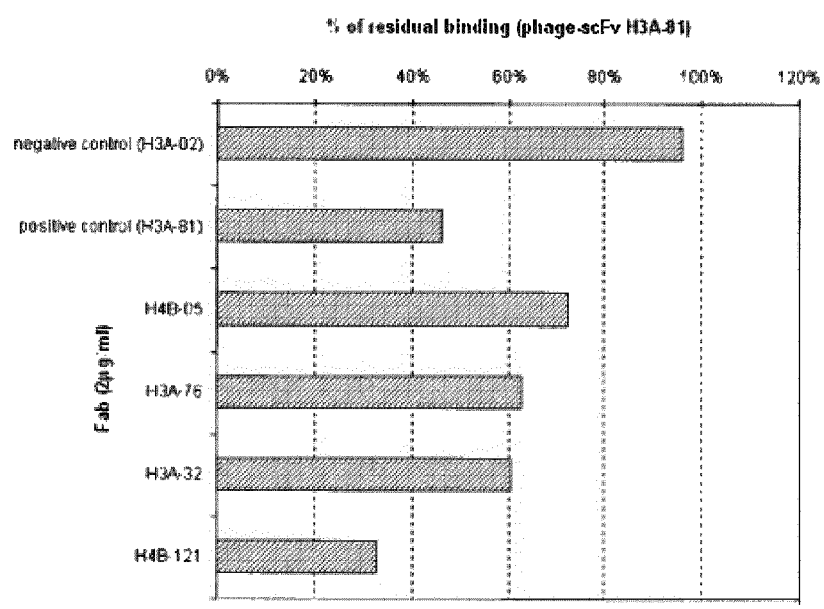

The FIG. 2 exhibits an overview of the competition for binding to HER3 between the phage-scFv clone H3A-81 versus each other Fabs. The residual binding of the phage-scFv-H3A-81 at a concentration of $1\times10^{-7}$ M of the competitor Fabs was assigned in percentage. The irrelevant Fab clone H3A-02 was used as negative control and the clone H3A-81 in the Fab format was used as positive control (competition to himself). As shown in FIG. 2, the clones H3A-81, H4B-05, H3A-76, H3A-32 and H4B-121 compete for HER3 binding with the clone H3A-81. This data suggests that these clones share the same epitope or have in common a same recognition area at the surface of the HER3 receptor.

Construction of Anti-HER3 IgG, Production and Characterization

Conversion in IgG format

The VH and VL regions of the human recombinant antibodies were assembled by overlapping PCR with appropriate leader sequences (human heavy chain leader or human light chain leader) and inserted into the vectors pMGM09-H (for Heavy chain expression) and pMGM09-Llambda (for Lambda Light chain expression) or pMGM09-Lkappa (for kappa Light chain expression). These eukaryotic expression systems permit the expression of the antibodies as an IgG1 isotype driven by a CMV promoter. The production of anti-HER3 IgG is achieved through the FreeStyle MAX Expression System (Invitrogen) using transient transfected human embryonic kidney 293 cells in suspension in serum-free medium. The IgG expression procedure was done according to the supplier's protocol in 24 (or 6)-well plates. Seven days after transfection, cells were centrifuged to recover supernatants containing antibodies. These human anti-HER3 antibodies were purified using standard protein A purification methods.

IgG Binding: Fully Human

Figure 3:
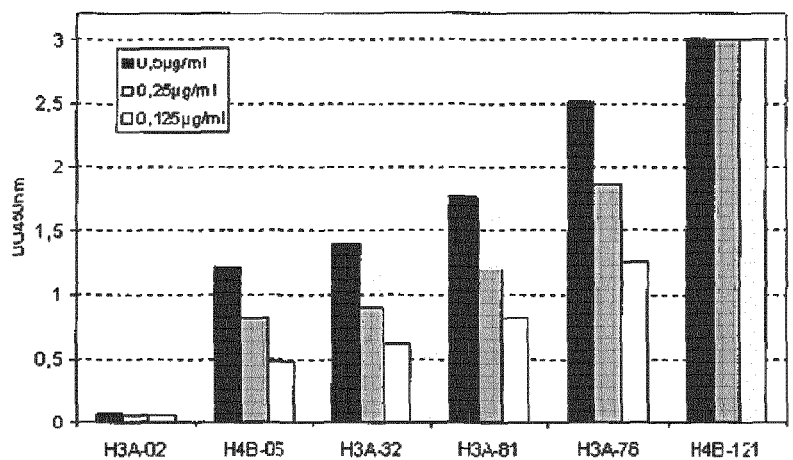
FIG. 3 shows the results of ELISA binding curves for the purified human IgG of the invention. The clone H3A-02 is an irrelevant antibody used as negative control.
Figure 4:
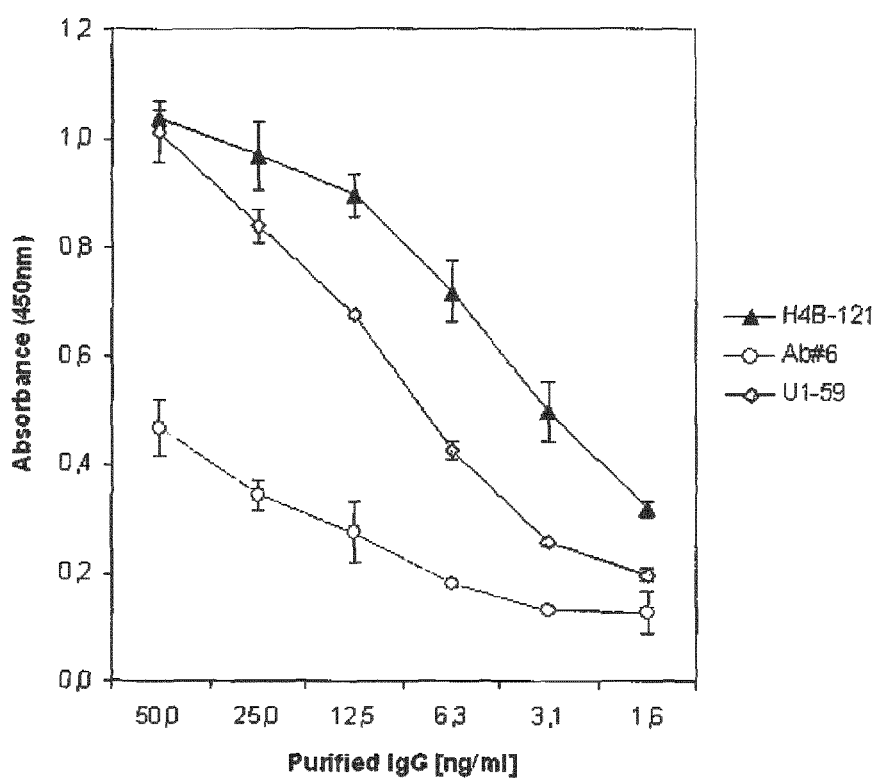
FIG. 4 shows the binding curves of the H4B-121 compared with two other anti-HER3 antibodies (Ab#6 and U1-59).

The purified human IgG anti-HER3 were incubated for 2 hours at 37° C. in coated wells at 50 ng human HER3-Fc (or HER4-Fc) at three concentrations: 0.5 μg/ml, 0.25 μg/ml, 0.125 μg/ml. The bound IgG were detected by using HRP-F (ab') 2 goat anti human IgG F(ab')2 specific (Interchim). All the IgG tested exhibit no cross-reactivity against HER4. As depicted in FIG. 3, the IgG anti-HER3 of the invention show distinct affinity binding to human HER3 and H4B-121 shows the strongest reactivity from this group of related antibodies. The antibody H4B-121 was compared with two others anti-HER3 antibodies Ab#6 (Merrimack Pharmaceuticals) and U1-59 (Amgen/U3 Pharma-Daiichi Sankyo). These antibodies U1-59 and Ab#6 were constructed based disclosure of sequences in patent US2008/0124345A1 and US2009/0291085A1 respectively. As shown in FIG. 4, the H4B-121 clearly exhibit better reactivity compared to Ab#6 and U1-59.

Cross-Reactivity with Mouse HER3 Receptor

Figure 5:
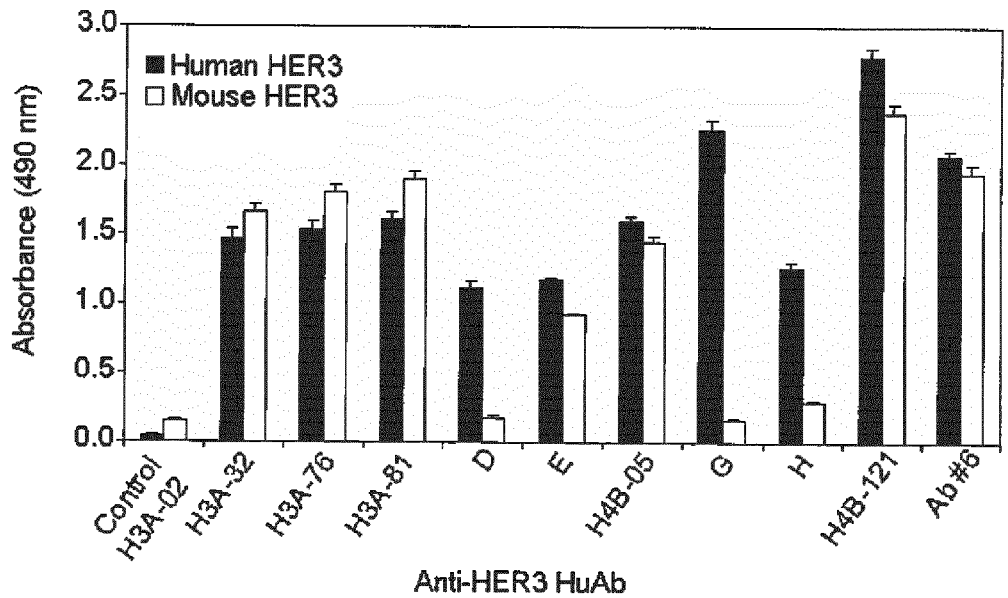
FIG. 5 shows the reactivity of the purified human IgG antibodies of the invention towards human HER3 vs mouse HER3. Antibodies D, E, G and H are positive control anti-HER3.
Figure 6:
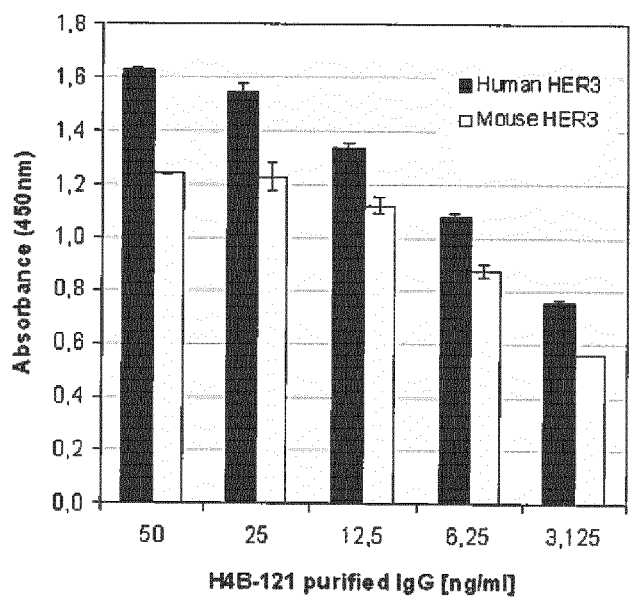
FIG. 6 shows the dose dependence reactivity of the H4B-121 antibody towards human HER3 and mouse HER3.

The cross-reactivity were assessed by a comparative ELISA assay with immobilized human HER3-Fc and mouse HER3-Fc (recombinant mouse extracellular domain ErbB3/HER3 Fc chimera, R&D Systems) coated at 250 ng/ml The five clones of the invention, at a concentration of 1 μg/ml cross reacted with mouse HER3 (FIG. 5) as well as the Ab#6 antibody. The clone H4B-121 is the best binder of this group of clones and FIG. 6 illustrated the dose dependence reactivity of H4B-121 with the human and mouse HER3 receptors. Irrelevant control antibody H3A-02 bound neither human nor mouse HER3.

Flow Cytometry Analysis to HER3-Positive Cells

Figure 7:
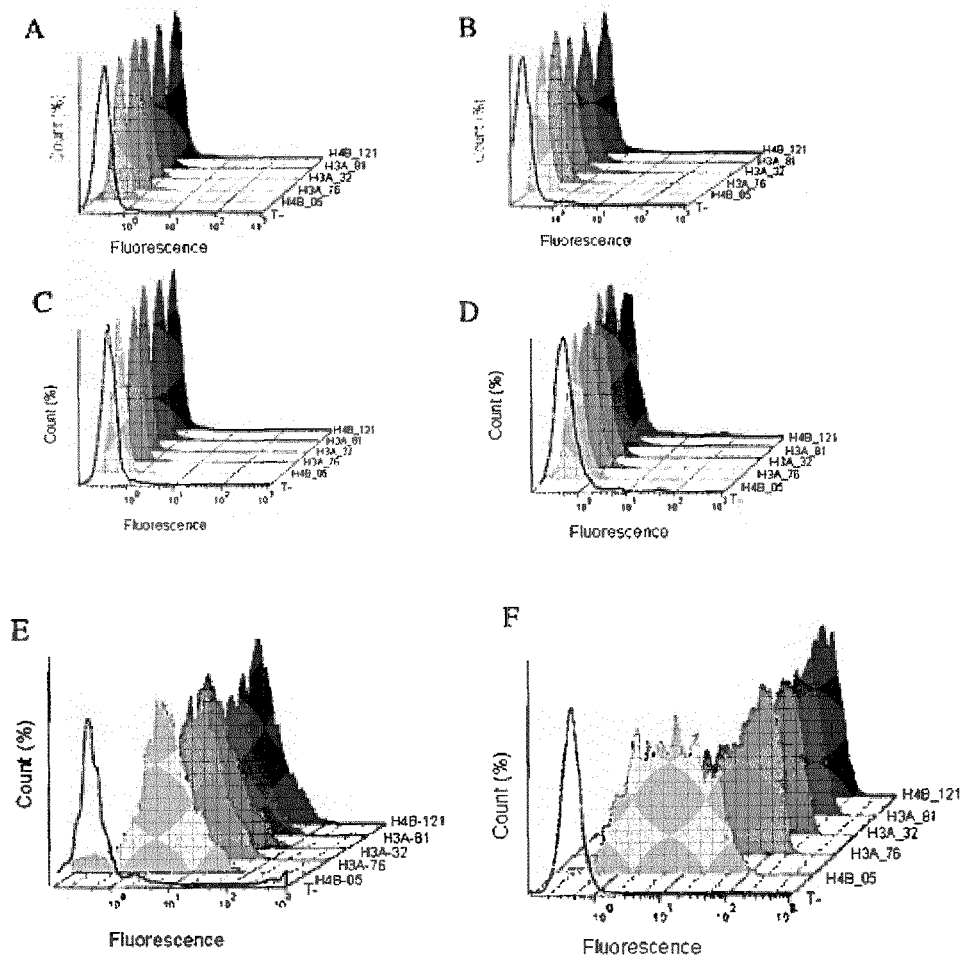

HER3- and HER2/HER3 complex-transfected NIH 3T3 fibroblasts ($10^6$ cells) were incubated with the purified human IgG anti-HER3 in PBS-BSA 0.1% at 4° C. for 1 h. After three washes in PBS-BSA 0.1%, cells were incubated with the fluorescein-conjugated anti-human IgG-Fragment Fc specific (Sigma) at 4° C. in the dark for 45 min. Cells were then washed three times and suspended in PBS for analysis using an EPICS flow cytometer (Beckman-Coulter, Fullerton, Calif.). As shown in FIG. 7, all the anti-HER3 human IgG; H3A-32, H3A-76, H3A-81, H4B-05 and H4B-121 bind to HER3- and HER2/HER3-transfected (FIGS. 7E and 7F), but not to wild-type NIH 3T3 cells (FIG. 7A). No binding was observed with control cells (EGFR, HER2 and EGFR/HER4 respectively FIGS. 7B, 7C and 7D). No binding was observed with the negative control antibody H3A-02 as well (T−). The antibodies of the invention were compared with the antibodies U1-59 and Ab#6 indicated above.

TABLE 10

Results of flow cytometry specific binding profile

| Ab Name | Wt NIH-3T3 | Transfected NIH-3T3 | | | | |
|---|---|---|---|---|---|---|
| | | EGFR | HER2 | HER3 | HER2/HER3 | EGFR/HER4 |
| H3A-02 | 0.39[a] | 0.24 | 0.49 | 0.50 | 0.49 | 0.60 |
| U1-59 | 0.45 | 0.25 | 0.42 | 9.32 | 15.5 | 0.59 |
| Ab#6 | 0.43 | 0.21 | 0.35 | 7.77 | 14.1 | 0.51 |
| H3A-32 | 0.47 | 0.26 | 0.44 | 10.5 | 68.8 | 0.53 |
| H3A-76 | 0.56 | 0.24 | 0.52 | 11.5 | 66.6 | 0.53 |
| H3A-81 | 0.55 | 0.26 | 0.50 | 10.6 | 68.5 | 0.53 |
| H4B-05 | 0.46 | 0.28 | 0.41 | 7.85 | 13.3 | 0.52 |
| H4B-121 | 0.70 | 0.33 | 0.56 | 12.3 | 70.4 | 0.67 |

[a]geometric mean

Competition with Ligand Heregulin Binding

Cytometry competition experiments were performed in order to quantify the ability of HRG to inhibit antibody binding to HER3 in a SKBR3 cell-based assay. To this end, $10^5$ SKBR3 cells were pre-incubated with various concentrations of the competing HRG ligand for 1.5 h on ice. After one washing with PBS-1% BSA, anti-HER3 antibodies, at concentration giving 50% maximal binding, were added to each well for 1 h on ice. In some experiments, HRG ligand and anti-HER3 antibodies were co-incubated for 2 h on ice. Cells were then washed and further incubated with a 1:60 dilution of appropriate FITC-conjugated secondary antibody (Sigma) for 45 min on ice, before cytometry analysis on a Quanta apparatus (Beckman-Coulter). H4B-121 antibody, as well as positive-control antibody D showed a HRG-dependent binding decrease to the HER3 receptor, demonstrating that surprisingly epitopes recognized by these antibodies could be impaired for antibody binding when HRG induces transconformation of active HER3 receptor for heterodimerization and further signalling (FIG. 8). In contrast positive-control antibody G did not compete with HRG binding. Inhibitory concentration of 50% binding ranged around 2.5 nM of HRG ligand. Similar results were obtained either by sequential or co-incubation of HRG with antibodies.

HER2-HER3 Heterodimer Analysis by TR-FRET

The TR-FRET assay was performed using the mouse anti-HER3 mAb 15D4-F2 labeled with Lumi4-terbium cryptate (donor) and the anti-HER2 antibody FRP5 conjugated to the d2 dye (acceptor) (Cisbio Bioassay). Cells were plated at $10^5$ per well in 96-well sterile black microplates in DMEM (without phenol red) for 24 h, then washed with KREBS buffer, fixed in 10% formalin for 2 min and washed once with KREBS buffer. After incubation with the labeled mAbs in KREBS buffer at 37° C. for 6 hours, cells were washed 4 times with KREBS buffer. The fluorescence of Lumi4 Tb and d2 were measured respectively at 620 and 665 nm (60 µs delay, 400 µs integration) upon 337 nm excitation using a Pherastar FS instrument.

The fluorescence of serial dilutions of Lumi4 Tb-labeled antibodies in KREBS buffer was simultaneously measured in the same microtiter plate, and the 665 nm emission was plotted against the 620 nm emission. The resulting curve was used to compute the 665 nm contribution from terbium (F665Tb) using the 620 nm emission (F620) of the samples. The TR-FRET signal was expressed as Delta F665(%)=100× Delta F665/F665Tb, with Delta F665=F665c–F665Tb. The 665 nm and 620 nm emissions from the samples were corrected for background as $F665c=F665_{sample}-F665_{background}$ and $F620c=F620_{sample}-F620_{background}$. The $F665_{background}$ and $F620_{background}$ values were obtained by measuring the fluorescence of a plate containing only reading buffer. The TR-FRET signal expressed as Delta F665(%) represents relative amount of HER2/HER3 dimers normalized to the level of HER2. The human IgG of the invention were incubated 30 minutes with the HER2-HER3-transfected NIH-3T3 cells at 0, 1, 10 and 100 µg/ml. After the treatment, cells were fixed in 10% formalin to immobilize the dimers and to avoid any modifications during the labelling step with the Lumi4-Tb and d2 antibodies.

The irrelevant mAb Px was used as a negative control. The anti-HER2 antibodies trastuzumab (Herceptin®; Roche/Genentech) and pertuzumab (Roche/Genentech) were used as positive control. Heregulin was used to confirm its ability to increase the concentration of HER2-HER3 heterodimer in this assay. As shown in FIG. 9, the anti-HER3 antibody H4B-121 inhibits the HER2-HER3 heterodimer formation from 1 µg/ml and furthermore in a ligand-independent manner (without heregulin stimulation).

Epitope Mapping Using SPOT Peptide Array

Membranes were obtained from Abimed (Langenfeld, Germany). Fmoc amino acids and N-hydroxybenzotriazole were obtained from Novabiochem (Läufelfingen, Switzerland). The ASP222 robot (Abimed) was used for the coupling steps. Two hundred-and-thirteen overlapping pentadecapeptides frameshifted by three residues, representing the extracellular domain of HER3 receptor, were synthesized on cellulose membranes. All peptides were acetylated at their N-terminus. After the peptide sequences were assembled, the side-chain protecting groups were removed by trifluoroacetic acid treatment. After three washings in TBS buffer (137 mM NaCl, 2.68 mM KCl, 50 mM Tris), the membrane was saturated with TBS buffer containing 0.1% Tween 20 (TBS-T) and 2% semi-skimmed milk for 18 h at 4° C. After one washing in TBS-T, a 1 µg/ml solution of the antibody H4B-121 was added to the membrane for 1 h30 at 37° C. Bound antibody was detected by incubation of the membrane at 37° C. for 1 h in a 1:10000 dilution of a peroxidase-conjugated anti-human F(ab')2 (Jackson ImmunoResearch), and subsequent electrochimioluminescent revelation. As shown in FIG. 10, two possible epitopes were recognized by H4B-121. A first area is delimitated by residues 214-231 in the domain 1, and a second peptide was identified comprising residues 343-357 in the domain 3 of the extracellular domain of HER3. Region 342-358 (SEQ ID NO: 35) was further confirmed in a second experiment by using overlapping pentadecapeptides frameshifted by only one or two residues (FIG. 11).

To precisely identify the epitope recognized by H4B-121 antibody, Spot alanine scanning analysis was performed, Thirty-nine pentadecapeptides corresponding to antibody-immunoreactive amino acid sequences previously identified, and the fifteen alanine analogs of each peptide were synthesized by the Spot method. Antibody reactivity of cellulose-bound peptides was assayed similarly as described above. The reactivity of the spots was evaluated by scanning the membrane and measuring the intensities of the spots with the Image J software 1.44 (http://rsbweb.nih.gov/ij). Spot Contributing Residues (SCR), belonging to the HER3 epitopes recognized by H4B-121 antibody were identified on the basis of decreased antibody-binding capacity equal or superior to 20% of that of the unmodified peptide sequence. Substituting Asp$^{352}$ of peptides $^{342}$LDFLITGLNGDPWHK$^{356}$, $^{343}$DFLITGLNGDPWHKI$^{357}$ and $^{344}$FLITGLNGDPWH-KIP$^{358}$ by an alanine residue led to a 92% decrease in H4B-121 binding capacity (FIG. 11). Similarly, replacement of Trp$^{354}$, His$^{355}$ and Lys$^{356}$ led to an almost complete loss of H4B-121 antibody reactivity whereas changing Pro$^{353}$ and Ile$^{357}$ only demonstrated 40 to 60%-decrease in antibody reactivity (FIG. 11). The nine other alanine replacements in the three pendadecapeptides 342-356, 343-357 and 344-358 from the HER3 receptor did not modify antibody-binding ability. Thus, the key binding motif for H4B-121 antibody from the HER3/D3 domain was determined to be $^{352}$DPWHKI$^{357}$ (SEQ ID NO: 36) with residues Asp$^{352}$, Trp$^{354}$, His$^{355}$ and Lys$^{356}$ being the main SCRs. Residues Trp$^{354}$, His$^{355}$ and Lys$^{356}$ are phylogenetically conserved among murine and monkey HER3, explaining why H4B-121 both bind to human and murine HER3 by ELISA (FIG. 4A), and suggesting that H4B-121 probably cross-reacted with rhesus monkey HER3 (Macaca mulatta). In contrast, sequence alignment with human EGFR, HER2 and HER4 receptors demonstrated amino-acid differences in HER3/D3 region 353-357, thus explaining why this antibody did not recognized other HER family receptors by flow cytometry. We performed positioning of SCRs from the binding motif of H4B-121 antibody on the crystallographic structure of unliganded HER3 receptor (pdb 1M6B). H4B-121 binding motif $^{352}$DPWHKI$^{357}$ (SEQ ID NO: 36) protruded at the junction between D2 and D3 domains, this binding motif overhanging the D2 domain. At present, no crystal structure of HER3 receptor bound to a ligand has been reported. By sequence homology, epitope recognized by HER3-specific antibody H4B-121 was superimposed on the crystallographic structure of the HER2 receptor bound to pertuzumab (pdb 1S78), thus indicated that the epitope is accessible even in the closed conformation of the HER3 receptor.

Tumor Growth Inhibition

Athymic, 6- to 8-week-old, female BALB/c nude mice were purchased from Janvier and Charles Rivers Laboratories. HER2-non amplified/PIK3CA-wt/p53-mut skin A431 ($1\times10^6$) and HER2-non amplified/PIK3CA-wt/p53-wt BxPC3 ($3.5\times10^6$) cancer cells were injected s.c. into the right flank of athymic BALB/c nude mice. They both expressed HER3 receptor at low level (between 10000 and 20000 receptors/cell). In add, A431 cancer cells secreted HER3 ligand HRG and are HRG-addicted (Yonesaka, 2011).

Tumor-bearing mice were randomized in the different treatment groups when the tumors reached an approximate volume of 100 mm$^3$. The mice were treated by i.p. injections with 0.9% NaCl of HER3-specific H4B-121 antibody. The amount of injected antibody was 300 μg/injection, three-time week (Q2d, 15 mg/kg), for 6 weeks consecutively. Tumor dimensions were measured twice weekly with a caliper and the volumes were calculated by the formula D1×D2×D3/2. Tumor progression was calculated using the formula [(final volume)−(initial volume)]/(initial volume). The results were also expressed by a Kaplan-Meier survival curve, using the time taken for the tumor to reach a determined final volume of 2,000 mm$^3$. A median delay was defined as the time at which 50% of the mice had a tumor reaching the determined volume. As shown in FIG. 12A, the administration of 300 μg (Q2d) of the human antibody H4B-121 results in a significant inhibition of tumor growth. At day 31 post-implantation (corresponding to 20 days after the beginning of the treatment), anti-HER3 antibody H4B-121 inhibited significantly tumor growth by approximately 53±6% in mice xenografted with A431 cancer cells, compared with vehicle control (FIG. 12A). The median delay to reach a tumor size of 2,000 mm3 is increased by 14 days (FIG. 12B), with regard to the treatment with the control vehicle (NaCl) (42 days) versus H4B-121 treatment (56 days). As shown in FIG. 13A, we observed a significant 68±4%-reduction in pancreatic BxPC3 tumor growth in antibody-treated mice at day 56 post-tumor implantation (corresponding to 26 days after the beginning of antibody treatment), with regard to tumor size measured in mice treated with vehicle (p<0.001). At the end of the experiment (135 days), Kaplan-Meier analysis revealed an 18-day delay in 50%-mean survival time for pancreatic BxPC3-xenografted mice treated with H4B-121 antibody (FIG. 13B). In this case (FIG. 13B, inside), tumors extracted from H4B-121-treated mice demonstrated an inhibition of Tyr1289 HER3 phosphorylation and a downregulation of the HER3 receptor, with regard to tumors extracted from vehicle-treated mice.

Inhibition of Phosphorylation and Internalization of the HER3 Receptor

Five hundred and thousand BxPC3 tumor cells were added to each well of a 6-well culture plate for 24 h at 37° C. After serum starvation for 16 h in a RPMI complete medium with 1% FCS and further washing, cells were pre-incubated with a 50 μg/l concentration of H4B-121 antibody, negative control Px antibody or Ab#6 antibody for 1 h at 37° C., before washing and subsequent stimulating or not with a 100 ng/ml dilution of heregulin. Cells were then washed, scraped and lysed with buffer containing 20 mM Tris-HCl pH 7.5, 150 mM NaCl, 1.5 mM MgCl$_2$, 1 mM EDTA, 1% Triton, 10% glycerol, 0.1 mM Phenylmethylsulfonyl fluoride, 100 mM sodium fluoride, 1 mM sodium orthovanadate (Sigma-Aldrich), and one complete protease inhibitor mixture tablet (Roche Diagnostics, Indianapolis, Ind.). After a 30 min-incubation time, samples were cleared of insoluble fraction by centrifugation and protein concentrations in cell lysates were determined by Bradford assay. These protein lysates were directly mixed with Laemmli buffer (1-20 μg total proteins depending on the target and cell lines) and heated at 95° C. for 5 minutes. After electrophoresis on 7% SDS-PAGE under reducing conditions, the proteins were transferred to polyvinylidene difluoride membranes (Millipore) which were then saturated in TNT buffer (Tris 25 mM pH 7.4, NaCl 150 mM, Tween 0.1%) containing 5% nonfat dry milk for 1 h at 25° C. Primary antibodies, directed to kinase receptors or signaling kinases, and their phosphorylated forms, were incubated in TNT-5% BSA buffer for 18 h at 4° C. After five washes in TNT buffer, peroxidase-conjugated rabbit, goat or mouse polyclonal antibodies (Sigma-Aldrich) were added as appropriate in TNT buffer containing 5% nonfat dry milk for 1 h at 25° C. After five washes in TNT buffer, the blots were visualized using a chemiluminescent substrate (Western lightning Plus-ECL, Perkin Elmer).

Remarkably, D3-specific antibody H4B-121 blocked ligand-induced phosphorylation at Tyr1289 residue on HER3. Inhibition of Akt phosphorylation on Ser473 and Thr308 was concomitantly demonstrated following a 15 min short-time treatment of antibodies on BxPC3 cells. Phosphorylation of AKT-triggered downstream signalling was also affected by H4B-121 antibody, i.e. inhibition of the phosphorylation of phospho-S6 ribosomal protein which reduces protein synthesis, blockade of phosphorylation of FoxO1a which favors gene nuclear transcription leading to apoptosis and cell cycle arrest, decrease of phospho-MDM2 which prevents p53 degradation, and inhibition of phospho-GSK3 which blocks the cell cycle.

BxPC3 cells were analyzed for cell surface expression of HER2 and HER3 receptors after exposure to H4B-121 antibody for different times and temperatures. As shown on FIG. 14A, a 2h-antibody incubation of BxPC3 cells at 37° C. strongly reduced HER3 cell surface expression, but did not affect EGFR and HER2 receptors (FIG. 14A). Antibody-induced HER3 down-regulation was abrogated when cells were treated at 4° C., thus demonstrating that HER3-specific antibody H4B-121 induced HER3 internalization. Quantification of HER3 internalization demonstrated that H4B-121 is more efficient than Ab#6 to induce HER3 internalization (FIG. 14B).

REFERENCES

Throughout this application, various references describe the state of the art to which this invention pertains. The disclosures of these references are hereby incorporated by reference into the present disclosure.

Brady G, Jantzen H M, Bernard H U, Brown R, Schutz G, Hashimoto-Gotoh T. New cosmid vectors developed for eukaryotic DNA cloning. Gene. 1984 February; 27(2):223-32.

Campiglio M, All S, Knyazev P G, Ullrich A. Characteristics of EGFR family-mediated HRG signals in human ovarian cancer. J Cell Biochem. 1999 Jun. 15; 73(4):522-32.

Campbell M R, Amin D, Moasser M M. HER3 comes of age: new insights into its functions and role in signaling, tumor biology, and cancer therapy. Clin Cancer Res. 2010 Mar. 1; 16(5):1373-83. Epub 2010 Feb. 23.

Caron P C, Laird W, Co M S, Avdalovic N M, Queen C, Scheinberg D A. Engineered humanized dimeric forms of IgG are more effective antibodies. J Exp Med. 1992 Oct. 1; 176(4):1191-5.

Citri A, Yarden Y. EGF-ERBB signalling: towards the systems level. Nat Rev Mol Cell Biol. 2006 July; 7(7):505-16.

Edge A S, Faltynek C R, Hof L, Reichert L E Jr, Weber P. Deglycosylation of glycoproteins by trifluoromethane-sulfonic acid. Anal Biochem. 1981 Nov. 15; 118(1):131-7.

Gillies S D, Morrison S L, Oi V T, Tonegawa S. A tissue-specific transcription enhancer element is located in the major intron of a rearranged immunoglobulin heavy chain gene. Cell. 1983 July; 33(3):717-28.

Hynes N E, Lane H A. ERBB receptors and cancer: the complexity of targeted inhibitors. Nat Rev Cancer. 2005 May; 5(5):341-54.

Hynes N E, Stern D F. The biology of erbB-2/neu/HER-2 and its role in cancer. Biochim Biophys Acta. 1994 Dec. 30; 1198(2-3):165-84.

Karamouzis M V, Badra F A, Papavassiliou A G. Breast cancer: the upgraded role of HER-3 and HER-4. Int J Biochem Cell Biol. 2007; 39(5):851-6. Epub 2006 Dec. 27.

Kim H H, Vijapurkar U, Hellyer N J, Bravo D, Koland J G. Signal transduction by epidermal growth factor and heregulin via the kinase-deficient ErbB3 protein. Biochem J. 1998 Aug. 15; 334 (Pt 1):189-95.

Kruser T J, Wheeler D L. Mechanisms of resistance to HER family targeting antibodies. Exp Cell Res. 2010 Apr. 15; 316(7):1083-100. Epub 2010 Jan. 11.

Kuwana Y, Asakura Y, Utsunomiya N, Nakanishi M, Arata Y, Itoh S, Nagase F, Kurosawa Y. Expression of chimeric receptor composed of immunoglobulin-derived V regions and T-cell receptor-derived C regions. Biochem Biophys Res Commun. 1987 Dec. 31; 149(3):960-8.

Lee-Hoeflich S T, Crocker L, Yao E, Pham T, Munroe X, Hoeflich K P, Sliwkowski M X, Stern H M. A central role for HER3 in HER2-amplified breast cancer: implications for targeted therapy. Cancer Res. 2008 Jul. 15; 68(14): 5878-87.

Mason J O, Williams G T, Neuberger M S. Transcription cell type specificity is conferred by an immunoglobulin VH gene promoter that includes a functional consensus sequence. Cell. 1985 June; 41(2):479-87.

Menendez J A, Mehmi I, Lupu R. Trastuzumab in combination with heregulin-activated Her-2 (erbB-2) triggers a receptor-enhanced chemosensitivity effect in the absence of Her-2 overexpression. J Clin Oncol. 2006 Aug. 10; 24(23):3735-46.

Miyaji H, Mizukami T, Hosoi S, Sato S, Fujiyoshi N, Itoh S. Expression of human beta-interferon in Namalwa KJM-1 which was adapted to serum-free medium. Cytotechnology. 1990 March; 3(2):133-40.

Mizukami T, Itoh S. A new SV40-based vector developed for cDNA expression in animal cells. J Biochem (Tokyo). 1987 May; 101(5):1307-10.

Morrison S L, Johnson M J, Herzenberg L A, Oi V T. Chimeric human antibody molecules: mouse antigen-binding domains with human constant region domains. Proc Natl Acad Sci USA. 1984 November; 81(21):6851-5.

Naidu R, Yadav M, Nair S, Kutty M K. Expression of c-erbB3 protein in primary breast carcinomas. Br J Cancer. 1998 November; 78(10):1385-90.

Neuberger M S, Williams G T, Fox R O. Recombinant antibodies possessing novel effector functions. Nature. 1984 Dec. 13-19; 312(5995):604-8.

O'Hare K, Benoist C, Breathnach R. Transformation of mouse fibroblasts to methotrexate resistance by a recombinant plasmid expressing a prokaryotic dihydrofolate reductase. Proc Natl Acad Sci USA. 1981 March; 78(3): 1527-31.

Padlan E A. A possible procedure for reducing the immunogenicity of antibody variable domains while preserving their ligand-binding properties. Mol Immunol. 1991 April-May; 28(4-5):489-98.

Plowman G D, Whitney G S, Neubauer M G, Green J M, McDonald V L, Todaro G J, Shoyab M. Molecular cloning and expression of an additional epidermal growth factor receptor-related gene. Proc Natl Acad Sci USA. 1990 July; 87(13):4905-9.

Riechmann L, Clark M, Waldmann H, Winter G Reshaping human antibodies for therapy. Nature. 1988 Mar. 24; 332 (6162):323-7.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994 Feb. 1; 91(3):969-73.

Shitara K, Nakamura K, Tokutake-Tanaka Y, Fukushima M, Hanai N. A new vector for the high level expression of chimeric antibodies in myeloma cells. J Immunol Methods. 1994 Jan. 3; 167(1-2):271-8.

Shopes B. A genetically engineered human IgG mutant with enhanced cytolytic activity. J Immunol. 1992 May 1; 148 (9):2918-22.

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994 June; 7(6): 805-14.

Thotakura N R, Bahl O P. Enzymatic deglycosylation of glycoproteins. Methods Enzymol. 1987; 138:350-9.

Travis A, Pinder S E, Robertson J F, Bell J A, Wencyk P, Gullick W J, Nicholson R I, Poller D N, Blarney R W, Elston C W, Ellis 10. C-erbB-3 in human breast carcinoma: expression and relation to prognosis and established prognostic indicators. Br J Cancer. 1996 July; 74(2):229-33.

Urlaub G, Chasin L A. Isolation of Chinese hamster cell mutants deficient in dihydrofolate reductase activity. Proc Natl Acad Sci USA. 1980 July; 77(7):4216-20.

The invention claimed is:

1. An anti-HER3 antibody comprising:
   (i) a heavy chain wherein the variable domain comprises:
      SEQ ID NO: 1 for H-CDR1,
      SEQ ID NO: 2 for H-CDR2, and
      SEQ ID NO: 3 for H-CDR3; and
   (ii) a light chain in which the variable domain comprises:
      L-CDR1 selected from the group consisting of SEQ ID NO:4, SEQ ID NO: 11, SEQ ID NO: 18, SEQ ID NO: 25 and SEQ ID NO: 29,
      L-CDR2 selected from the group consisting of SEQ ID NO:5, SEQ ID NO: 12 and SEQ ID NO: 19 and
      L-CDR3 selected from the group consisting of SEQ ID NO:6, SEQ ID NO: 13, SEQ ID NO: 20 and SEQ ID NO: 26.

2. The antibody according to claim 1, wherein the heavy chain variable domain has the amino acid sequence selected from the group consisting of SEQ ID NO: 7, SEQ ID NO: 14 and SEQ ID NO: 21.

3. The antibody according to claim 1 wherein the light chain variable domain has an amino acid sequence selected from the group consisting of SEQ ID NO: 8, SEQ ID NO: 15, SEQ ID NO: 22, SEQ ID NO: 27 and SEQ ID NO: 30.

4. The antibody according to claim 1 wherein said antibody is selected from the group consisting of:
   an antibody comprising the heavy chain variable domain having the amino acid sequence set forth as SEQ ID NO: 7, and the light chain variable domain having the amino acid sequence selected from the group consisting of SEQ ID NO: 8 and SEQ ID NO: 30,
   an antibody comprising the heavy chain variable domain having the amino acid sequence set forth as SEQ ID NO: 14, and the light chain variable domain having the amino acid sequence selected from the group consisting of SEQ ID NO: 15 and SEQ ID NO: 27 and
   an antibody comprising the heavy chain variable domain having the amino acid sequence set forth as SEQ ID NO: 21, and the light chain variable domain having the amino acid sequence selected from the group consisting of SEQ ID NO: 22.

5. The antibody according to claim 1 wherein said antibody is a human antibody.

6. The antibody according to claim 1 wherein said antibody is an antibody fragment selected from the group consisting of Fv, Fab, F(ab')2, Fab', dsFv, scFv, sc(Fv)2 and diabodies.

7. A nucleic acid comprising a sequence encoding at least the heavy chain and the light chain of the antibody according to claim 1.

8. A vector comprising a nucleic acid according to claim 7.

9. A host cell comprising a nucleic acid according to claim 7.

10. A host cell comprising a vector according to claim 8.

11. A pharmaceutical composition comprising an antibody according to claim 1 and a pharmaceutically acceptable carrier.

12. A method of treating cancer in a subject in need thereof comprising
   administering to said subject a therapeutically effective amount of the antibody of claim 1.

* * * * *